US012629037B2

(12) United States Patent
   Fan et al.

(10) Patent No.: US 12,629,037 B2
(45) Date of Patent: May 19, 2026

(54) AUDIOPLETHYSMOGRAPHY CALIBRATION

(71) Applicant: Google LLC, Mountain View, CA (US)

(72) Inventors: Xiaoran Fan, Irvine, CA (US); Trausti Thormundsson, Irvine, CA (US)

(73) Assignee: Google LLC, Mountain View, CA (US)

( * ) Notice: Subject to any disclaimer, the term of this patent is extended or adjusted under 35 U.S.C. 154(b) by 330 days.

(21) Appl. No.: 18/556,843

(22) PCT Filed: Jun. 9, 2023

(86) PCT No.: PCT/US2023/068208
   § 371 (c)(1),
   (2) Date: Oct. 23, 2023

(87) PCT Pub. No.: WO2023/240240
   PCT Pub. Date: Dec. 14, 2023

(65) Prior Publication Data
   US 2025/0082210 A1      Mar. 13, 2025

Related U.S. Application Data

(60) Provisional application No. 63/366,219, filed on Jun. 10, 2022.

(51) Int. Cl.
   *A61B 5/0205*      (2006.01)
   *A61B 5/00*      (2006.01)
(52) U.S. Cl.
   CPC .......... *A61B 5/0205* (2013.01); *A61B 5/6817* (2013.01); *A61B 5/7225* (2013.01)
(58) Field of Classification Search
   None
   See application file for complete search history.

(56) References Cited

U.S. PATENT DOCUMENTS

| | | | | |
|---|---|---|---|---|
| 5,105,822 A | * | 4/1992 | Stevens ................... | A61B 5/12 |
| | | | | 73/587 |
| 7,354,380 B2 | | 4/2008 | Volpe | |

(Continued)

FOREIGN PATENT DOCUMENTS

| | | |
|---|---|---|
| JP | 2018500949 A | 1/2018 |
| JP | 2022056790 A | 4/2022 |

(Continued)

OTHER PUBLICATIONS

"International Search Report and Written Opinion", Application No. PCT/US2023/064242, Nov. 3, 2023, 21 pages.

(Continued)

*Primary Examiner* — Stephanie E Bloss
*Assistant Examiner* — Diana Hancock
(74) *Attorney, Agent, or Firm* — Colby Nipper PLLC

(57)      ABSTRACT

Techniques and apparatuses are described that perform audioplethysmography calibration. Provided according to one or more preferred embodiments is a hearable, such as an earbud, that is capable of performing a novel physiological monitoring process termed herein audioplethysmography, an active acoustic method capable of sensing subtle physiologically-related changes observable at a user's outer and middle ear. The hearable can utilize audioplethysmography to monitor a user's biometrics, recognize facial behaviors, and/or sense an environment using acoustic signals. The techniques for audioplethysmography calibration enable the hearable to dynamically select frequencies that improve the performance of audioplethysmography. With audioplethysmography calibration, the hearable may utilize different frequencies for different ears and these frequencies may change over time.

20 Claims, 18 Drawing Sheets

1200

Transmit an acoustic transmit signal that propagates within at least a portion of an ear canal of a user
1202

Receive an acoustic receive signal, the acoustic receive signal representing a version of the acoustic transmit signal with one or more waveform characteristics modified due to the propagation within the ear canal
1204

Determine at least one physiological metric of the user based on the one or more modified characteristics of the acoustic receive signal
1206

(56)  References Cited

U.S. PATENT DOCUMENTS

| | | | | |
|---|---|---|---|---|
| 10,873,798 | B1 | 12/2020 | Jackson et al. | |
| 11,402,902 | B2 | 8/2022 | Parshionikar | |
| 12,042,328 | B2* | 7/2024 | Arakawa | A61B 5/0245 |
| 12,495,980 | B2 | 12/2025 | Fan et al. | |
| 2004/0196992 | A1 | 10/2004 | Ryan | |
| 2009/0097689 | A1 | 4/2009 | Prest et al. | |
| 2010/0125218 | A1 | 5/2010 | Haartsen et al. | |
| 2010/0189269 | A1 | 7/2010 | Haartsen et al. | |
| 2014/0051940 | A1* | 2/2014 | Messerschmidt | A61B 5/6815 |
| | | | | 600/509 |
| 2019/0022348 | A1 | 1/2019 | Read et al. | |
| 2019/0294769 | A1 | 9/2019 | Lesso | |
| 2020/0186910 | A1 | 6/2020 | Kemmerer et al. | |
| 2020/0187795 | A1 | 6/2020 | Yokoi et al. | |
| 2020/0196977 | A1 | 6/2020 | Martin et al. | |
| 2021/0186426 | A1 | 6/2021 | Raju et al. | |
| 2021/0275056 | A1 | 9/2021 | Mcmahon et al. | |
| 2021/0281943 | A1 | 9/2021 | Lehnert | |
| 2022/0087570 | A1 | 3/2022 | Lesso et al. | |
| 2022/0183659 | A1 | 6/2022 | Margalit | |
| 2022/0386959 | A1 | 12/2022 | Georgiou et al. | |
| 2023/0096953 | A1 | 3/2023 | Kuster et al. | |
| 2024/0307022 | A1* | 9/2024 | Fan | A61B 5/02405 |
| 2024/0312478 | A1* | 9/2024 | Fan | H04R 1/1016 |
| 2025/0082300 | A1* | 3/2025 | Fan | A61B 8/5223 |
| 2025/0213142 | A1* | 7/2025 | Amihood | A61B 8/12 |
| 2025/0278240 | A1* | 9/2025 | Amihood | G01S 15/88 |
| 2025/0318800 | A1* | 10/2025 | Fan | A61B 5/6803 |

FOREIGN PATENT DOCUMENTS

| | | | | |
|---|---|---|---|---|
| WO | 2010054863 | | 5/2010 | |
| WO | 2015076916 | | 5/2015 | |
| WO | 2016150947 | | 9/2016 | |
| WO | 2019018750 | | 1/2019 | |
| WO | 2019152212 | | 8/2019 | |
| WO | 2019226739 | A1 | 11/2019 | |
| WO | 2020082387 | A1 | 4/2020 | |
| WO | 2020130535 | A1 | 6/2020 | |
| WO | 2020174680 | A1 | 9/2020 | |
| WO | 2021123720 | | 6/2021 | |
| WO | WO-2021123720 | A1* | 6/2021 | H04R 29/00 |
| WO | 2022019442 | A1 | 1/2022 | |
| WO | 2023240224 | | 12/2023 | |
| WO | 2023240233 | | 12/2023 | |
| WO | 2024191456 | A1 | 9/2024 | |
| WO | 2024191491 | A1 | 9/2024 | |
| WO | 2024192250 | A1 | 9/2024 | |
| WO | 2024192386 | A1 | 9/2024 | |

OTHER PUBLICATIONS

Amesaka, et al., "Facial Expression Recognition Using Ear Canal Transfer Function", Sep. 19, 2019, 9 pages.
"International Preliminary Report on Patentability", Application No. PCT/US2023/068198, Dec. 10, 2024, 6 pages.
"International Preliminary Report on Patentability", Application No. PCT/US2023/068181, Dec. 10, 2024, 7 pages.
"International Preliminary Report on Patentability", Application No. PCT/US2023/068208, Dec. 10, 2024, 7 pages.
"Extended European Search Report", Application No. 24163311.4, Jun. 18, 2024, 11 pages.
"Extended European Search Report", EP Application No. 24162019. 4, Jun. 18, 2024, 11 pages.
"International Search Report and Written Opinion", Application No. PCT/US2024/019953, Jul. 4, 2024, 13 pages.
"Invitation to Pay Additional Fees and Partial Search Report", Application No. PCT/US2024/020238, Jul. 11, 2024, 11 pages.
"Two AirPods Max Patents reveal the addition of a new processor and sensors designed to Detect Heart Pathologies", Retrieved at: https://www.patentlyapple.com/2024/03/two-airpods-max-patents-reveal-the-addition-of-a-new-processor-and-sensors-designed-to-detect-heart-pathologies.html—on Jun. 12, 2024, 12 pages.

"A Research Space for Earable Computing", Retrieved at: https://www.esense.io/—on May 10, 2022, 16 pages.
"Air—Speed of Sound vs. Temperature", Retrieved at: https://www.engineeringtoolbox.com/air-speed-sound-d_603. html—on May 10, 2022, 14 pages.
"Cardioid XLR Lav Microphone", Retrieved at: https://www.movophoto.com/products/lv4-c-xlr-phantom-power-lav-cardioid-mic—on May 10, 2022, 3 pages.
"Finger Pulse Oximeter, (SpO2) Blood Oxygen Saturation Monitor with Pulse Rate Measurements and Pulse Bar Graph, Digital Reading LED Display", Retrieved at: https://santamedical.com/collections/oximeters/products/finger-pulse-oximeter-spo2-blood-oxygen-saturation-monitor-with-pulse-rate-measurements-and-pulse-bar-graph-digital-reading-led-display—on May 10, 2022, 4 pages.
"International Search Report and Written Opinion", Application No. PCT/US2023/068198, Aug. 31, 2023, 10 pages.
"International Search Report and Written Opinion", Application No. PCT/US2023/068208, Aug. 31, 2023, 11 pages.
"International Search Report and Written Opinion", Application No. PCT/US2023/068181, Sep. 4, 2023, 11 pages.
"Invitation to Pay Additional Fees and Partial Search Report", Application No. PCT/US2023/064242, Sep. 20, 2023, 13 pages.
"Speed of Sound in Gases", Retrieved at: https://www.betamachinery.com/knowledge-center/speed-of-sound-in-gases-list—on May 10, 2022, 4 pages.
"What is Carbon Dioxide?", Retrieved at: https://www.co2meter.com/blogs/news/10709101-what-is-carbon-dioxide, Dec. 9, 2013, 6 pages.
Appelhans, et al., "Heart Rate Variability as an Index of Regulated Emotional Responding", Sep. 2006, pp. 229-240.
Bui, et al., "eBP: A Wearable System For Frequent and Comfortable Blood Pressure Monitoring From User's Ear", Oct. 2019, 17 pages.
Butkow, et al., "Motion-resilient Heart Rate Monitoring with In-ear Microphones", Aug. 2021, 14 pages.
Chamary, JV, "You'll Be Surprised How Often You Actually Touch Your Face", https://www.forbes.com/sites/jvchamary/2020/07/30/coronavirus-face-touching/?sh=442158ae375f, Jul. 30, 2020, 6 pages.
Fan, et al., "Enabling Low-Cost Full Surface Tactile Skin for Human Robot Interaction", Apr. 2022, pp. 1800-1807.
Fan, et al., "HeadFi: Bringing Intelligence to All Headphones", Oct. 2021, 14 pages.
Geisler, et al., "The impact of heart rate variability on subjective well-being is mediated by emotion regulation", Nov. 2010, pp. 723-728.
He, et al., "An Ear-worn Continuous Ballistocardiogram (BCG) Sensor for Cardiovascular Monitoring", Apr. 2015, 15 pages.
Lane, et al., "Neural correlates of heart rate variability during emotion", Jan. 2009, pp. 213-222.
Laskowski, Edwardr. , "What's a normal resting heart rate?", Oct. 2, 2020, 4 pages.
Lofqvist, et al., "Speed of Sound Measurements in Gas-Mixtures at Varying Composition Using an Ultrasonic Gas Flow Meter with Silicon Based Transducers", Jan. 1, 2003, 6 pages.
Ma, et al., "OESense: Employing Occlusion Effect for In-ear Human Sensing", Jun. 16, 2021, 13 pages.
Martin, et al., "In-Ear Audio Wearable: Measurement of Heart and Breathing Rates for Health and Safety Monitoring", Jun. 2018, pp. 1256-1263.
Moller, et al., "Transfer Characteristics of Headphones Measured on Human Ears", Apr. 1995, 16 pages.
Nguyen, et al., "A Lightweight And Inexpensive In-ear Sensing System For Automatic Whole-night Sleep Stage Monitoring", Nov. 2016, 15 pages.
Poh, et al., "Cardiovascular monitoring using earphones and a mobile device", Dec. 2012, 9 pages.
Poh, et al., "Heartphones: Sensor Earphones and Mobile Application for Non-obtrusive Health Monitoring", Sep. 2009, pp. 153-154.
Rahman, et al., "How Frequently Do We Touch Facial T-Zone: A Systematic Review", https://www.annalsofglobalhealth.org/articles/10.5334/aogh.2956/, Jul. 6, 2020, 9 pages.
Roddiger, et al., "Towards Respiration Rate Monitoring Using an In-Ear Headphone Inertial Measurement Unit", Sep. 2019, 7 pages.

(56)                    References Cited

OTHER PUBLICATIONS

Rupavatharam, et al., "Towards In-Ear Inertial Jaw Clenching Detection", Sep. 2019, pp. 54-55.

Schafer, Ronaldw. , "What is a Savitzky-Golay Filter", Jul. 2011, 7 pages.

Shilko, et al., "Calculation of Pulse Wave Parameters with Account of Blood Vessel Deformation", Jan. 2001, pp. 88-94.

Sissons, Claire, "What to know about patulous eustachian tube", Jun. 12, 2020, 10 pages.

Stein, Phyllisk. , "Heart rate variability: a measure of cardiac autonomic tone", May 1994, pp. 1376-1381.

Vogel, et al., "In-Ear Vital Signs Monitoring Using a Novel Microoptic Reflective Sensor", Nov. 2009, pp. 882-889.

Wallburg, Kris, "Control Your AirPods with a Wink or Smile", https://www.macworld.com/article/675759/patent-control-your-airpods-with-a-wink-or-smile.html, Dec. 2, 2020, 4 pages.

Winokur, et al., "A Wearable Vital Signs Monitor at the Ear for Continuous Heart Rate and Pulse Transit Time Measurements", Apr. 15, 2015, 14 pages.

Winokur, et al., "A Wearable Vital Signs Monitor at the Ear for Continuous Heart Rate and Pulse Transit Time Measurements", Sep. 2012, pp. 2724-2727.

Wong, George, "Speed of Sound in Standard Air", Jan. 28, 1986, 8 pages.

Zhao, et al., "Emotion Recognition using Wireless Signals", Oct. 2016, 14 pages.

"International Search Report and Written Opinion", Application No. PCT/US2023/086447, Apr. 12, 2024, 14 pages.

Jin, et al., "EarCommand "Hearing" Your Silent Speech Commands In Ear", Jul. 7, 2022, 28 pages.

Nguyen, et al., "A Scalable and Domain Adaptive Respiratory Symptoms Detection Framework using Earables", Dec. 2021, 6 pages.

Roddiger, et al., "Sensing with Earables", Sep. 7, 2022, 57 pages.

Zhang, et al., "Coughtrigger: Earbuds IMU Based Cough Detection Activator using an Energy-efficient Sensitivity-prioritized Time Series Classifier", May 2022, 5 pages.

Zhang, et al., "EarCough: Enabling Continuous Subject Cough Event Detection on Hearables", Mar. 18, 2023, 6 pages.

"Foreign Office Action", EP Application No. 24162019.4, Apr. 8, 2025, 6 pages.

"Foreign Office Action", EP Application No. 23738398.9, May 21, 2025, 9 pages.

"International Preliminary Report on Patentability", Application No. PCT/US2023/086447, Sep. 10, 2025, 10 pages.

"International Preliminary Report on Patentability", Application No. PCT/US2024/020238, Sep. 10, 2025, 16 pages.

"International Preliminary Report on Patentability", Application No. PCT/US2024/019953, Sep. 10, 2025, 9 pages.

"Notice of Allowance", U.S. Appl. No. 18/602,888, Oct. 15, 2025, 17 pages.

"Restriction Requirement", U.S. Appl. No. 18/602,888, Aug. 7, 2025, 6 pages.

"Restriction Requirement", U.S. Appl. No. 18/556,853, Oct. 30, 2025, 8 pages.

"International Search Report and Written Opinion", Application No. PCT/US2024/020238, Oct. 2, 2024, 21 pages.

"Foreign Office Action", JP Application No. 2024-571923, Nov. 25, 2025, 13 pages.

"Foreign Office Action", EP Application No. 23739040.6, Mar. 2, 2026, 5 pages.

* cited by examiner

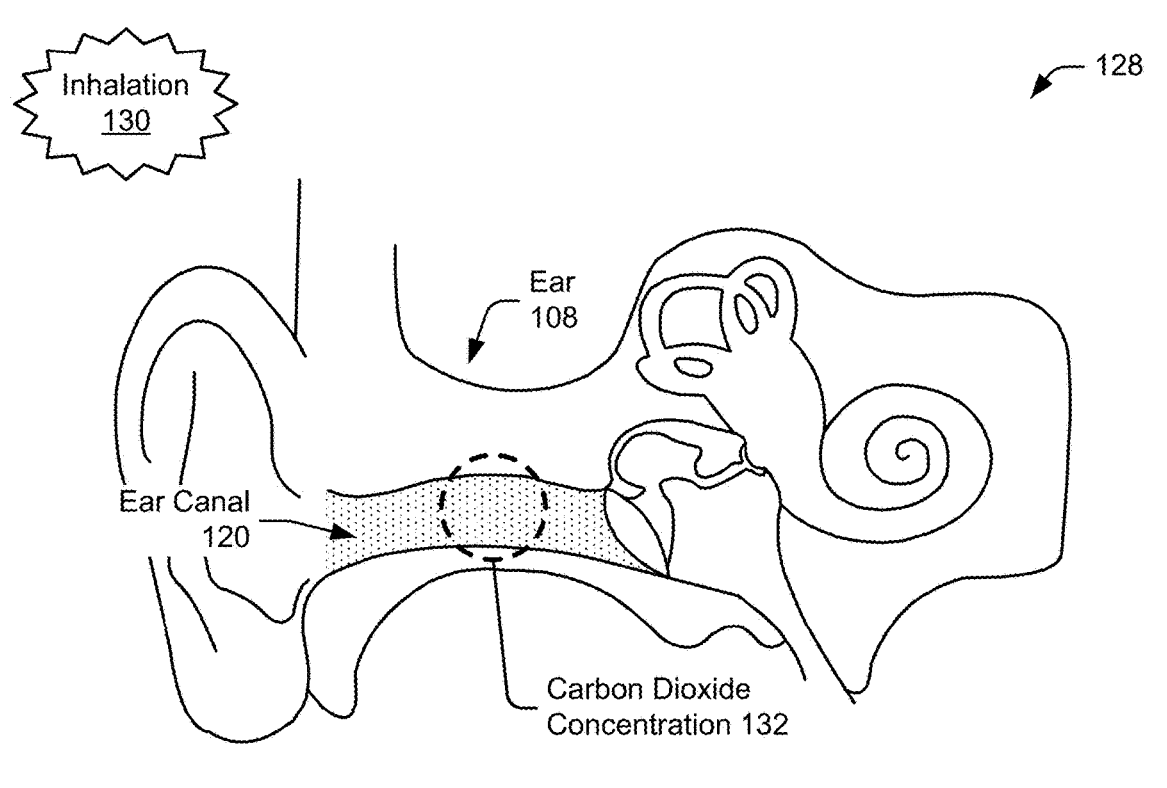
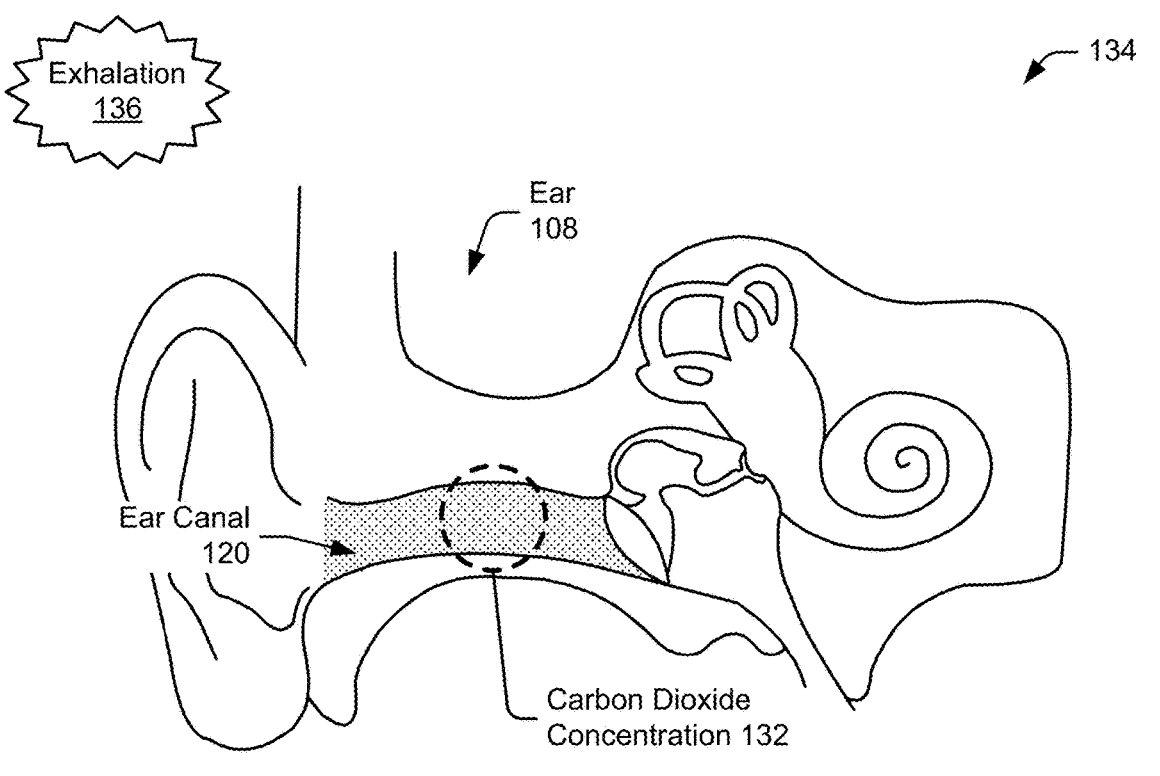
*FIG. 1-3*

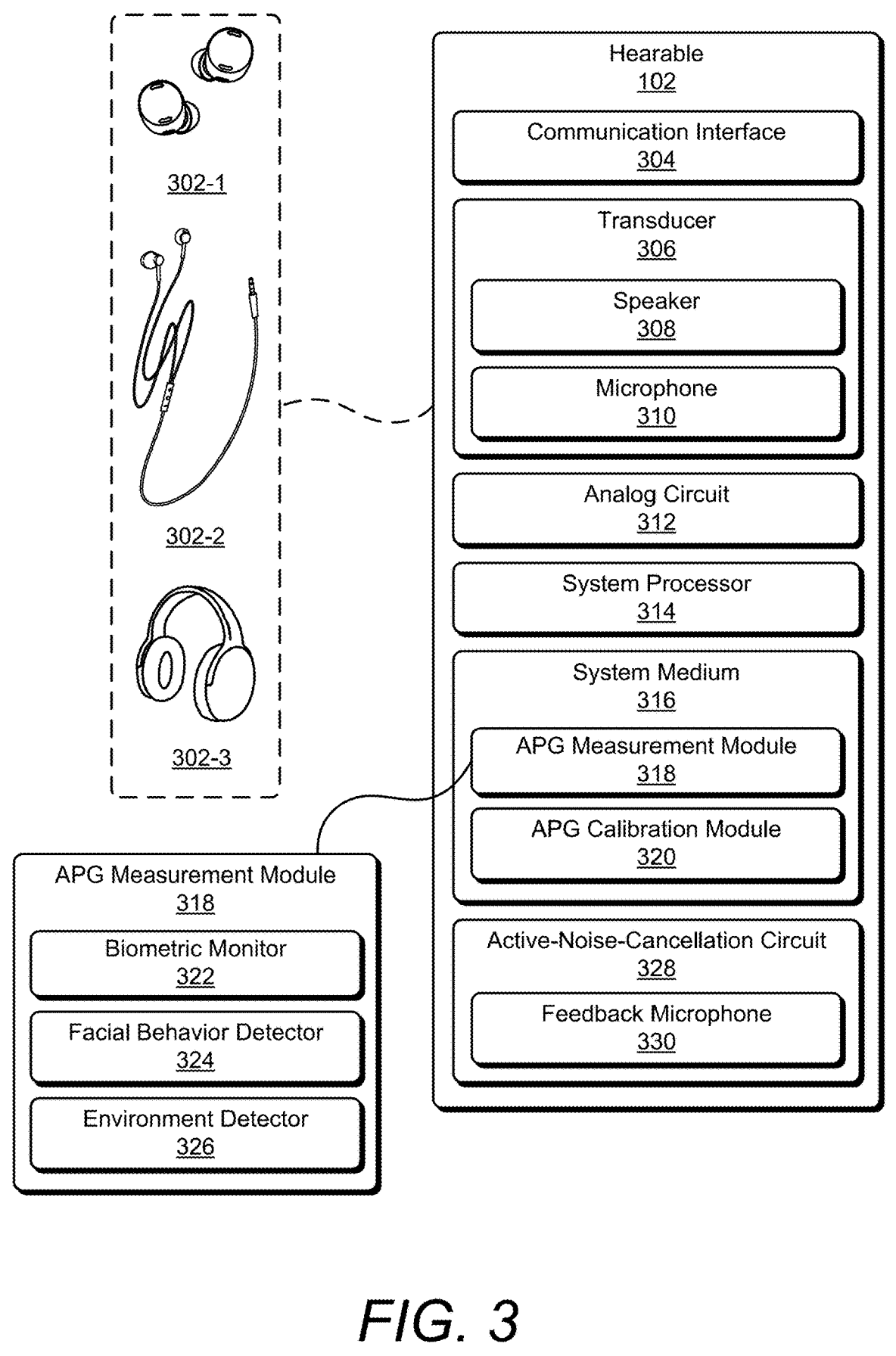

302-1

302-2

302-3

Hearable
102

Communication Interface
304

Transducer
306

Speaker
308

Microphone
310

Analog Circuit
312

System Processor
314

System Medium
316

APG Measurement Module
318

APG Calibration Module
320

Active-Noise-Cancellation Circuit
328

Feedback Microphone
330

APG Measurement Module
318

Biometric Monitor
322

Facial Behavior Detector
324

Environment Detector
326

FIG. 3

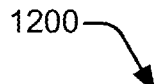

1200

Transmit an acoustic transmit signal that propagates
within at least a portion of an ear canal of a user
1202

Receive an acoustic receive signal, the acoustic receive
signal representing a version of the acoustic transmit
signal with one or more waveform characteristics
modified due to the propagation within the ear canal
1204

Determine at least one physiological metric of
the user based on the one or more modified
characteristics of the acoustic receive signal
1206

Figure 13:
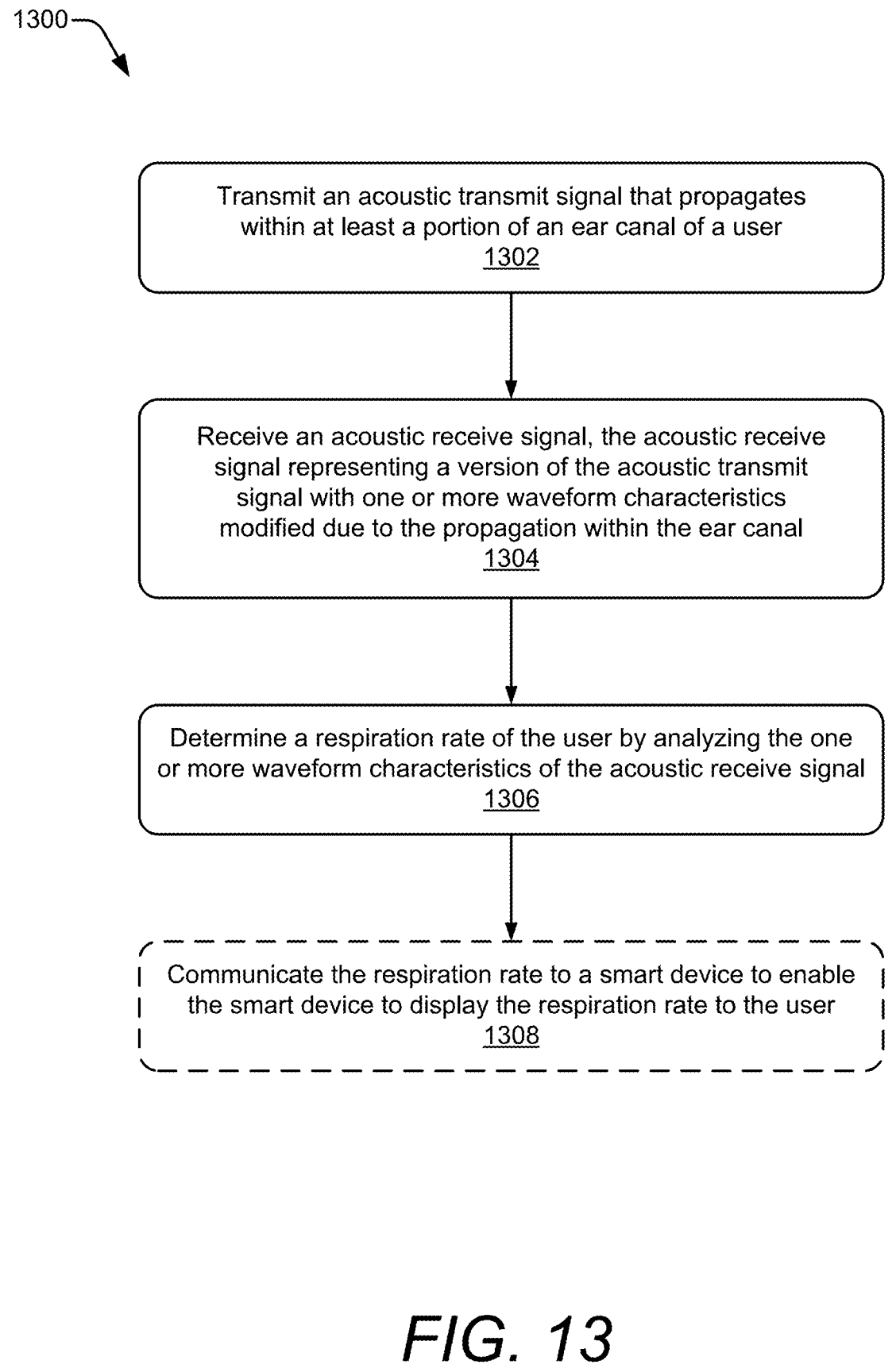

Transmit an acoustic transmit signal that propagates within at least a portion of an ear canal of a user
1302

Receive an acoustic receive signal, the acoustic receive signal representing a version of the acoustic transmit signal with one or more waveform characteristics modified due to the propagation within the ear canal
1304

Determine a respiration rate of the user by analyzing the one or more waveform characteristics of the acoustic receive signal
1306

Communicate the respiration rate to a smart device to enable the smart device to display the respiration rate to the user
1308

Perform a calibration process that identifies at least
one acoustic frequency suitable for audioplethysmography
using at least one speaker and at least one microphone
1402

Using the at least one acoustic frequency for performing
the audioplethysmography at an ear of a user
1404

AUDIOPLETHYSMOGRAPHY CALIBRATION

RELATED APPLICATION(S)

This application is a national stage entry of International Application No. PCT/US2023/068208, filed Jun. 9, 2023, which claims the benefit of U.S. Provisional Application No. 63/366,219, filed Jun. 10, 2022, the disclosures of which are incorporated herein by reference in their entirety.

BACKGROUND

Technological advances in medicine and healthcare are making it possible for people to live longer, healthier lives. To further achieve this, individuals have become interested in tracking their personal health. Health monitoring can motivate an individual to realize a particular fitness goal by tracking incremental improvements in the performance of the body's functions. Additionally, the individual can monitor the impact of various chronic illnesses on their body. With active feedback through health monitoring, the individual can live an active and full life with many chronic illnesses and quickly recognize situations in which it is necessary to seek medical attention.

Some devices that support health monitoring, however, can be obtrusive and uncomfortable. As such, people may choose to forego health monitoring if the device negatively impacts their movement or causes inconveniences while performing daily activities. It is therefore desirable for health-monitoring devices to be reliable, portable, and affordable to encourage more users to take advantage of these features.

SUMMARY

Techniques and apparatuses are described that implement audioplethysmography calibration.

Aspects described below include a method for audioplethysmography calibration. The method includes performing a calibration process that identifies at least one acoustic frequency suitable for audioplethysmography using at least one speaker and at least one microphone. The method also includes using the at least one frequency for performing the audioplethysmography at an ear of a user.

Some frequencies can be more sensitive for audioplethysmography than others. These frequencies can change over time based on the quality of an at least partial seal formed by a device at or around a user's ear. Also, these frequencies can vary for different ears of the user due to differences in the geometry of the ear canals. Techniques for audioplethysmography calibration as disclosed herein may therefore enable to dynamically select frequencies that improve the performance of audioplethysmography. With audioplethysmography calibration, different frequencies for different ears may be utilized, wherein these frequencies may change over time.

After calibration, an acoustic transmit signal that propagates within at least a portion of an ear canal of a user may be transmitted by at least one speaker. An acoustic receive signal may then be received by at least one microphone which acoustic receive signal represents a version of the acoustic transmit signal with one or more waveform characteristics modified due to the propagation within the ear canal. At least one physiological metric of the user may be determined based on the one or more modified waveform characteristics of the acoustic receive signal. Example waveform characteristics include amplitude, phase, and/or frequency. Generally, the acoustic receive signal may result from the initially transmitted acoustic transmit signal that is influenced with respect to at least one of its amplitude, phase and frequency when propagating within the ear canal before being received via the at least one microphone.

Aspects described below include a device comprising at least one transducer and at least one processor. The device is configured to perform any of the described methods.

Aspects described below also include a system with means for performing audioplethysmography calibration.

Provided according to one or more preferred embodiments is a hearable, such as an earbud, that is capable of performing a novel physiological monitoring process termed herein audioplethysmography, an active acoustic method capable of sensing subtle physiologically-related changes observable at a user's outer and middle ear. To better perform audioplethysmography, the hearable may form at least a partial seal in or around the user's outer ear. This seal enables formation of an acoustic circuit, which includes the seal, at least one hearable, at least one ear canal, and at least one ear drum of at least one ear. By transmitting and receiving acoustic signals, the hearable can recognize changes in the acoustic circuit to monitor a user's biometrics, recognize facial behaviors, and/or sense an environment. The hearable can be a standalone device or can be integrated within another object or device, such as glasses, a hat, ear muffs, or a helmet.

BRIEF DESCRIPTION OF DRAWINGS

Apparatuses for and techniques that facilitate audioplethysmography calibration are described with reference to the following drawings. The same numbers are used throughout the drawings to reference like features and components:

FIG. 1-2 illustrates an example geometric change in an ear canal, which can be detected using audioplethysmography;

FIG. 1-3 illustrates an example gas-composition change in an ear canal, which can be detected using audioplethysmography;

FIG. 2 illustrates an example implementation of a smart device;

FIG. 3 illustrates an example implementation of a hearable;

FIG. 4-1 illustrates example operations of two hearables performing single-ear audioplethysmography;

FIG. 4-2 illustrates an example joint operation of two hearables performing two-ear audioplethysmography;

FIG. 12 illustrates a first example method for performing an aspect of audioplethysmography;

FIG. 13 illustrates a second example method for performing an aspect of audioplethysmography;

DETAILED DESCRIPTION

Figure 1:
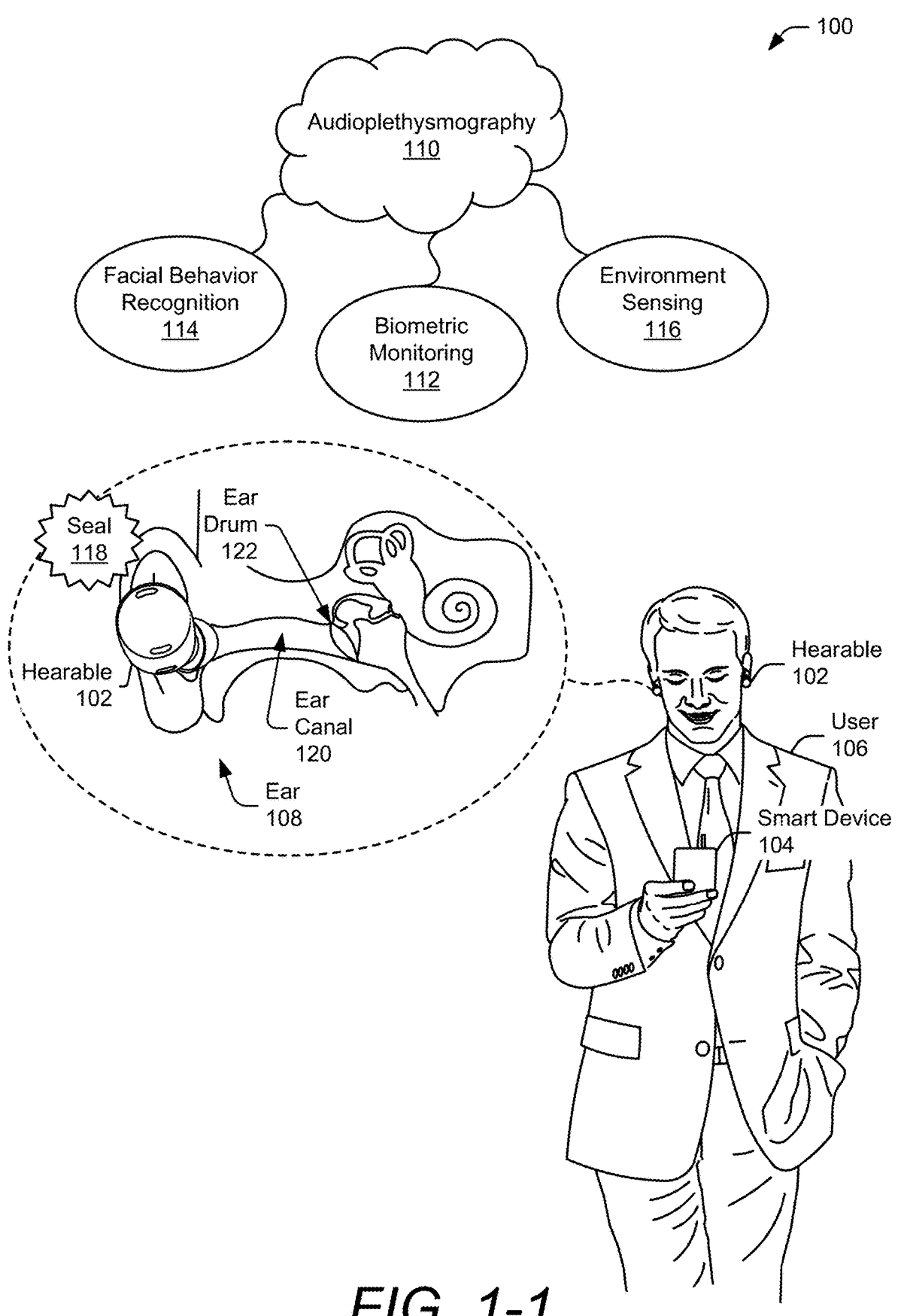
FIG. 1-1 illustrates an example environment in which audioplethysmography can be implemented.
Figure 1:
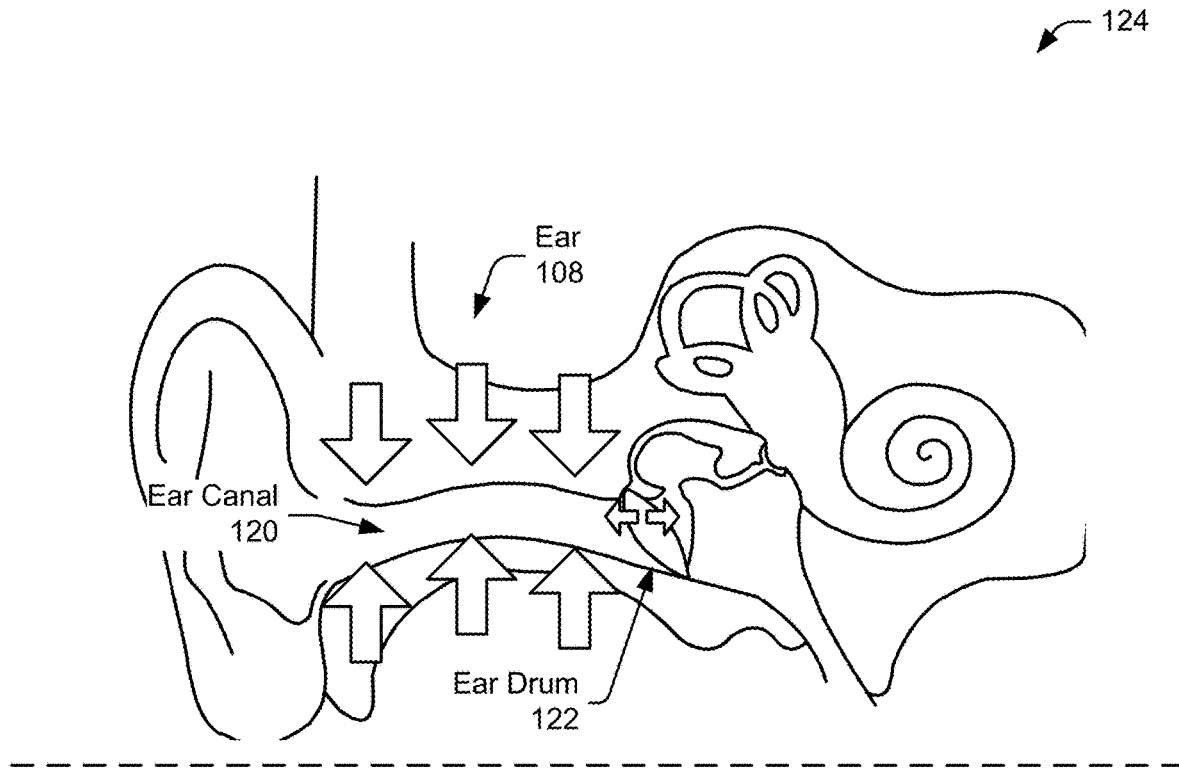

Technological advances in medicine and healthcare are making it possible for people to live longer, healthier lives. To further achieve this, individuals have become interested in tracking their personal health. Health monitoring can motivate an individual to realize a particular fitness goal by tracking incremental improvements in the performance of the body's functions. Additionally, the individual can use health monitoring to observe changes in the body caused by chronic illnesses. With active feedback through health monitoring, the individual can live an active and full life with many chronic illnesses and recognize situations in which it is necessary to quickly seek medical attention.

Some health monitoring devices, however, can be obtrusive and uncomfortable. To measure carbon dioxide levels, for example, some devices take a sample of blood from the user. Other devices may utilize auxiliary sensors, including optical or electronic sensors, that add additional weight, cost, complexity, and/or bulk. Still other devices may require constant recharging of a battery due to relatively high power usage. As such, people may choose to forego health monitoring if the health monitoring device negatively impacts their movement or causes inconveniences while performing daily activities. It is therefore desirable for health monitoring devices to be reliable, portable, efficient, and affordable to expand accessibility to more users.

To address this challenge and provide new features, in particular for existing hearables, techniques are described that implement audioplethysmography calibration. Provided according to one or more preferred embodiments is a hearable, such as an earbud, that is capable of performing a novel physiological monitoring process termed herein audioplethysmography, an active acoustic method capable of sensing subtle physiologically-related changes observable at a user's outer and middle ear. To better perform audioplethysmography, the hearable may form at least a partial seal in or around the user's outer ear. This seal enables formation of an acoustic circuit, which includes the seal, at least one hearable, at least one ear canal, and at least one ear drum of at least one ear. By transmitting and receiving acoustic signals, the hearable can recognize changes in the acoustic circuit to monitor a user's biometrics, recognize facial behaviors, and/or sense an environment.

Some frequencies can be more sensitive for audioplethysmography than others. These frequencies can change over time, in particular based on the quality of a seal formed by a hearable at or around a user's ear. Also, these frequencies can vary for different ears of the user due to differences in the geometry of the ear canals. The techniques for audioplethysmography calibration therefore enable the dynamic selection of frequencies that improve the performance of audioplethysmography. With audioplethysmography calibration, different frequencies for different ears may be utilized, wherein these frequencies may change over time.

Wireless technology has become prevalent in everyday life, making communication and data readily accessible to users. One type of wireless technology are wireless hearables, examples of which include wireless earbuds and wireless headphones. Wireless hearables have allowed users freedom of movement while listening to audio content from music, audio books, podcasts, and videos. With the prevalence of wireless hearables, there is a market for adding additional features to existing hearables utilizing current hardware (e.g., without introducing any new hardware). Accordingly, the proposed solution may in particular implemented by a wireless hearable. The proposed solution may also be implemented by other objects or devices with one or more built-in hearables, such as glasses, a hat, ear muffs, or a helmet.

Operating Environment

FIG. 1-1 is an illustration of an example environment 100 in which audioplethysmography calibration can be implemented. In the example environment 100, a hearable 102 is connected to a smart device 104 using a physical or wireless interface. The hearable 102 is a device that can play audible content provided by the smart device 104 and direct the audible content into a user 106's ear 108. In this example, the hearable 102 operates together with the smart device 104. In other examples, the hearable 102 can operate or be implemented as a stand-alone device. Although depicted as a smartphone, the smart device 104 can include other types of devices, including those described with respect to FIG. 2.

The hearable 102 is capable of performing audioplethysmography 110, which is an acoustic method of sensing that occurs at the ear 108. The hearable 102 can perform this sensing based on an evaluation of the transmitted and received acoustic signals alone and thus without the use of other auxiliary sensors, such as an optical sensor or an electrical sensor. Through audioplethysmography 110, the hearable 102 can perform biometric monitoring 112, facial behavior recognition 114, and/or environment sensing 116.

To use audioplethysmography 110, the user 106 positions the hearable 102 in a manner that creates at least a partial seal 118 around or in the ear 108. Some parts of the ear 108 are shown in FIG. 1, including an ear canal 120 and an ear drum 122 (or tympanic membrane). Due to the seal 118, the hearable 102, the ear canal 120, and the ear drum 122 couple together to form an acoustic circuit. Audioplethysmography 110 involves, at least in part, measuring properties associated with this acoustic circuit. The properties of the acoustic circuit can change due to a variety of different situations or actions.

Figure 2:
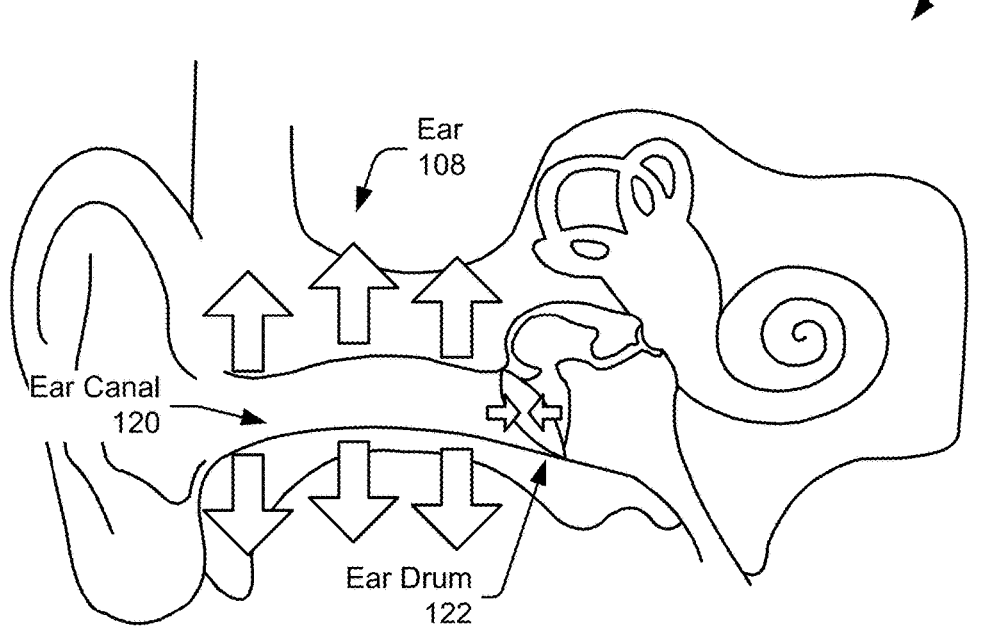
Figure 2:
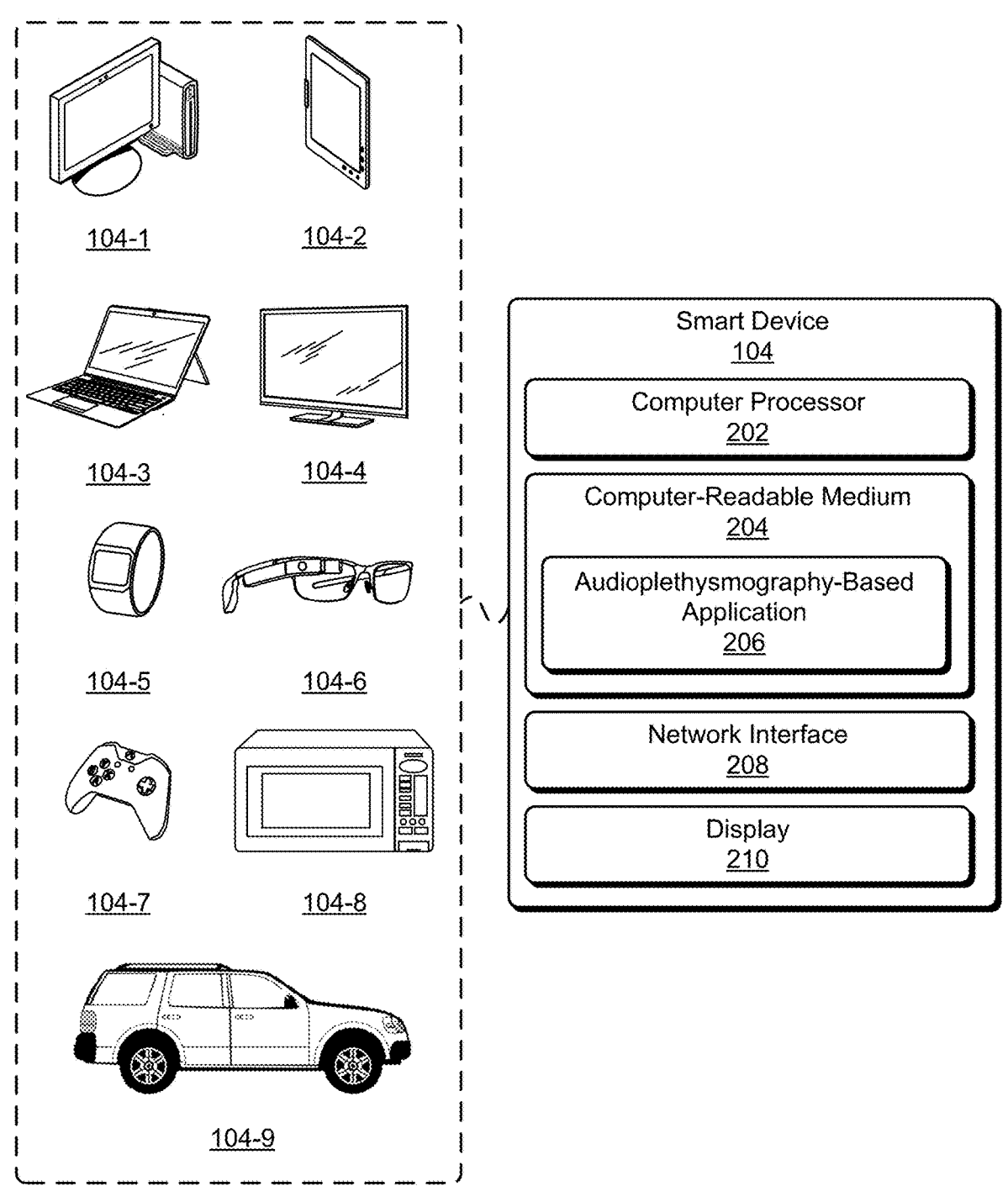

For example, consider FIG. 1-2 in which a change occurs in a physical structure of the ear 108. Example changes to the physical structure include a change in a geometric shape of the ear canal 120 and/or a change in a volume of the ear canal 120. This change can be caused, at least in part, by subtle blood vessel deformations in the ear canal 120 caused by the user 106's heart pumping. Other changes can also be caused by movement in the ear drum 122 or movement of the user 106's jaw.

At 124, for instance, the tissue around the ear canal 120 and the ear drum 122 itself are slightly "squeezed" due to blood vessel deformation. This squeeze causes a volume of the ear canal 120 to be slightly reduced at 124. At 126, however, the squeezing subsides and the volume of the ear canal 120 is slightly increased relative to 124. The physical changes within the ear 108 can modulate an amplitude and/or phase of an acoustic signal that propagates through the ear canal 120, as further described below.

During audioplethysmography 110, the acoustic signal propagates through at least a portion of the ear canal 120. The hearable 102 can receive an acoustic signal that represents a superposition of multiple acoustic signals that propagate along different paths within the ear canal 120. Each path is associated with a delay (τ) and an amplitude (a). The delay and amplitude can vary over time due to the subtle changes that occur in the physical structure of the ear canal 120. The received acoustic signal can be represented by Equation 1:

$$S(t) = n + \sum_{i=1}^{N-1} a_i(t) \cos \left( \varphi_{ini} + \Omega_{fc}(t + \tau_i(t)) \right) \qquad \text{Equation 1}$$

where S(t) represents the received acoustic signal, n represents noise, $\varphi_{ini}$ represents a relative phase between the received acoustic signal and the transmitted acoustic signal, $\Omega_{fc}$ represents a frequency of the transmitted acoustic signal, and/represents a time vector. Cardiac activities of the user 106 can modulate the amplitude and phase of the receive acoustic signal, so that the received acoustic signal can also be described as further shown in Equation 2:

$$S(t) = n + (1 + h_{amp}(t)) \cos \left( h_{phase}(t) + \varphi_{ini} + + \Omega_{fc}(t) \right) \qquad \text{Equation 2}$$

where $h_{amp}(t)$ represents an amplitude modulator and $h_{phase}(t)$ represents a phase modulator. For example, the two time-varying functions $h_{amp}(t)$ and $h_{phase}(t)$ can depend on interactions between the hearable 102 and the ear 108 as well as the physiological activities of the user 106, in particular on cardiac activities. When relating to heart-rate-based modulations, one can, for example, assume that $h_{amp}(t) = k_a \sin(\varphi_{hr} + + \Omega_{hr}(t))$ and $h_{phase}(t) = k_p \sin(\varphi_{hr} + + \Omega_{hr}(t))$, wherein $k_a$ and $k_p$ are modulation intensity coefficients and $\Omega_{hr}$ is a frequency of a heart rate of the user. The interactions between the hearable 102 and the ear 108 as well as the physiological activities of the user 106 modulate the amplitude and phase of the received acoustic signal.

As another example, consider FIG. 1-3 in which a gas-composition change occurs in the ear canal 120. This change is caused, at least in part, through breathing. As the user 106 breathes, the user 106's skin can exchange gas with its surroundings. For instance, at 128, inhalation 130 occurs and the gas-cycling system within the ear canal 120 causes the carbon dioxide concentration 132 to decrease. At 134, exhalation 136 occurs and the gas-cycling system within the ear canal 120 causes the carbon dioxide concentration 132 to increase. This change in the carbon dioxide concentration 132 impacts the speed of sound, which in turn impacts a speed at which acoustic signals propagate through the ear canal 120.

Returning to FIG. 1-1, the hearable 102 can detect aspects associated with biometric monitoring 112, facial behavior recognition 114, and/or environment sensing 116 using audioplethysmography 110. In general, biometric monitoring 112 can include measuring the user 106's heart rate, respiration rate, blood pressure, body temperature, and/or carbon dioxide level. Additionally, biometric monitoring 112 can be used to measure a physical structure of the ear canal 120 and/or detect motions associated with concussive forces. Through biometric monitoring 112, the hearable 102 can enable the user 106 to track a fitness goal or monitor overall health. This can be especially beneficial in caring for elderly patients or providing remote patient care. Some types of biometric monitoring 112 may require different qualities of the seal 118. The heart rate, for instance, can be measured with relatively little seal 118 while the respiration rate may require a better seal 118.

Audioplethysmography 110 can also be used for facial behavior recognition 114, which can include detecting jaw clenching, recognizing the start of speech, and/or recognizing certain activities that involve the jaw (e.g., speaking or eating). Other types of facial behavior recognition 114 include recognizing facial expressions, tracking the user 106's gaze or head posture, and/or recognizing facial touch gestures. To provide some of these features, audioplethysmography 110 can analyze an acoustic channel formed between the left and right ears 108. This acoustic channel can be modified by the user 106's facial expressions, gaze, head posture, or touch. Through facial behavior recognition 114, the hearable 102 can facilitate communication with speech and hearing disabled persons and/or improve automatic speech recognition. Facial behavior recognition 114 also enables a more effortless user experience as a user 106 can control features of the hearable 102 and/or smart device 104 without touching the hearable 102.

The hearable 102 can also support environment sensing 116, which can include detecting a sports activity (e.g., walking or running). By detecting the sports activity, the hearable 102 can automatically increase the volume of audible content for the user 106 or play audible content from a playlist associated with a workout routine. As another example, the hearable 102 can also automatically detect when the user 106 places the hearable 102 proximate to their ear 108 and forms the seal 118. As such, the hearable 102 can automatically determine when to play or pause the audible content for the user 106 or when to perform biometric monitoring 112 or facial behavior recognition 114. The techniques for audioplethysmography 110 can be performed while the hearable 102 is playing audible content to the user 106. The smart device 104 is further described with respect to FIG. 2.

FIG. 2 illustrates an example smart device 104. The smart device 104 is illustrated with various non-limiting example devices including a desktop computer 104-1, a tablet 104-2, a laptop 104-3, a television 104-4, a computing watch 104-5, computing glasses 104-6, a gaming system 104-7, a microwave 104-8, and a vehicle 104-9. Other devices may also be used, such as a home service device, a smart speaker, a smart thermostat, a baby monitor, a Wi-Fi™ router, a drone, a trackpad, a drawing pad, a netbook, an e-reader, a home automation and control system, a wall display, and another home appliance. Note that the smart device 104 can be wearable, non-wearable but mobile, or relatively immobile (e.g., desktops and appliances).

The smart device 104 includes one or more computer processors 202 and at least one computer-readable medium 204, which includes memory media and storage media. Applications and/or an operating system (not shown) embodied as computer-readable instructions on the computer-readable medium 204 can be executed by the computer processor 202 to provide some of the functionalities described herein. The computer-readable medium 204 also includes an audioplethysmography-based application 206, which uses information provided by the hearable 102 to perform an action. Example actions can include displaying biometric data to the user 106 based on biometric monitoring 112, providing touch-free control of the smart device 104 based on facial behavior recognition 114, or changing the presentation of audible content based on environment sensing 116.

The smart device 104 can also include a network interface 208 for communicating data over wired, wireless, or optical networks. For example, the network interface 208 may communicate data over a local-area-network (LAN), a wireless local-area-network (WLAN), a personal-area-network (PAN), a wire-area-network (WAN), an intranet, the Internet, a peer-to-peer network, point-to-point network, a mesh network, Bluetooth™, and the like. The smart device 104 may also include the display 210. Although not explicitly shown, the hearable 102 can be integrated within the smart device 104, or can connect physically or wirelessly to the smart device 104. The hearable 102 is further described with respect to FIG. 3.

FIG. 3 illustrates an example hearable 102. The hearable 102 is illustrated with various non-limiting example devices, including wireless earbuds 302-1, wired earbuds 302-2, and headphones 302-3. The earbuds 302-1 and 302-2 are a type of in-ear device that fits into the ear canal 120. Each earbud 302-1 or 302-2 can represent a hearable 102. Headphones 302-3 can rest on top of or over the ears 108. The headphones 302-3 can represent closed-back headphones, open-back headphones, on-ear headphones, or over-ear headphones. Some headphones 302-3 include two hearables 102, which are physically packaged together. In this case, there is one hearable 102 for each ear 108. Other headphones 302-2, such as single-ear headphones 302-2, include one hearable 102. In some implementations, one or more hearables 102 are implemented within (or as part of) another device, such as a pair of glasses, a hat, ear muffs, or a helmet.

The hearable 102 includes a communication interface 304 to communicate with the smart device 104, though this need not be used when the hearable 102 is integrated within the smart device 104. The communication interface 304 can be a wired interface or a wireless interface, in which audio content is passed from the smart device 104 to the hearable 102. The hearable 102 can also use the communication interface 304 to pass data measured using audioplethysmography 110 to the smart device 104. In general, the data provided by the communication interface 304 is in a format usable by the audioplethysmography-based application 206. The communication interface 304 also enables the hearable 102 to communicate with another hearable 102. During bistatic sensing, for instance, the hearable 102 can use the communication interface 304 to coordinate with the other hearable 102 to support two-ear audioplethysmography 110, as further described with respect to FIG. 4-2. In particular, the transmitting hearable 102 can communicate timing and waveform information to the receiving hearable 102 to enable the receiving hearable 102 to appropriately demodulate a received acoustic signal.

The hearable 102 includes at least one speaker and at least one microphone, for example as parts of at least one transducer 306 that can convert electrical signals into sound waves. The same transducer 306 or a further transducer of the hearable 102 can also detect and convert sound waves into electrical signals. These sound waves may include ultrasonic frequencies and/or audible frequencies, either of which may be used for audioplethysmography 110. In particular, a frequency spectrum (e.g., range of frequencies) that the transducer 306 uses to generate an acoustic signal can include frequencies from a low-end of the audible range to a high-end of the ultrasonic range, e.g., between 20 hertz (Hz) to 2 megahertz (MHz). Other example frequency spectrums for audioplethysmography 110 can encompass frequencies between 20 Hz and 20 kilohertz (kHz), between 20 kHz and 2 MHz, between 20 and 60 kHz, or between 30 and 40 kHz.

In an example implementation, the transducer 306 has a monostatic topology. With this topology, the transducer 306 can convert the electrical signals into sound waves and convert sound waves into electrical signals (e.g., can transmit or receive acoustic signals). Example monostatic transducers may include piezoelectric transducers, capacitive transducers, and micro-machined ultrasonic transducers (MUTs) that use microelectromechanical systems (MEMS) technology.

Alternatively, the transducer 306 can be implemented with a bistatic topology, which includes multiple transducers that are physically separate. In this case, a first transducer converts the electrical signal into sound waves (e.g., transmits acoustic signals), and a second transducer converts sound waves into an electrical signal (e.g., receives the acoustic signals). An example bistatic topology can be implemented using at least one speaker 308 and at least one microphone 310. The speaker 308 and the microphone 310 can be dedicated for audioplethysmography 110 or can be used for both audioplethysmography 110 and other functions of the smart device 104 (e.g., presenting audible content to the user 106, capturing the user 106's voice for a phone call, or for voice control).

In general, the speaker 308 and the microphone 310 are directed towards the ear canal 120 (e.g., oriented towards the ear canal 120). Accordingly, the speaker 308 can direct acoustic signals towards the ear canal 120, and the microphone 310 is responsive to receiving acoustic signals from the direction associated with the ear canal 120.

The hearable 102 includes at least one analog circuit 312, which includes circuitry and logic for conditioning electrical signals in an analog domain. The analog circuit 312 can include analog-to-digital converters, digital-to-analog converters, amplifiers, filters, mixers, and switches for generating and modifying electrical signals. In some implementations, the analog circuit 312 includes other hardware circuitry associated with the speaker 308 or microphone 310.

The hearable 102 also includes at least one system processor 314 and at least one system medium 316 (e.g., one or more computer-readable storage media). In the depicted configuration, the system medium 316 includes an audioplethysmography measurement module 318 (APG measurement module 318) and optionally includes an audioplethysmography calibration module 320 (APG calibration module 320). The audioplethysmography measurement module 318 and the audioplethysmography calibration module 320 can be implemented using hardware, software, firmware, or a combination thereof. In this example, the system processor 216 implements the audioplethysmography measurement module 318 and the audioplethysmography calibration module 320. In an alternative example, the computer processor 202 of the smart device 104 can implement at least a portion of the audioplethysmography measurement module 318 and/or at least a portion of the audioplethysmography calibration module 320. In this case, the hearable 102 can communicate digital samples of the acoustic signals to the smart device 104 using the communication interface 304.

The audioplethysmography measurement module 318 analyzes receive acoustic signals to measure data associated with audioplethysmography 110. The audioplethysmography measurement module 318 can be implemented using at least one biometric monitor 322 for biometric monitoring 112, at least one facial behavior detector 324 for facial behavior recognition 114, and/or at least one environment detector 326 for environment sensing 116. Example audioplethysmography measurement modules 318 are further described with respect to FIGS. 5 and 7.

The audioplethysmography calibration module 320 can determine appropriate waveform characteristics for transmitting acoustic signals to improve audioplethysmography 110 performance. For example, the audioplethysmography calibration module 320 can take into account the quality of the seal 118 and the physical structure of the ear canal 120 to determine a transmission frequency that can enable the hearable 102 to detect the user 106's heart rate and/or respiration rate with an accuracy of 5% or less. With the audioplethysmography calibration module 320, the hearable 102 can dynamically adjust the transmission frequency each time the seal 118 is formed and based on the unique physical structure of each ear 108. Through this calibration process, the hearables 102 on different ears may operate with one or more different acoustic frequencies. An example implementation of the audioplethysmography calibration module 320 is further described with respect to FIG. 6.

Some hearables 102 include an active-noise-cancellation circuit 328, which enables the hearables 102 to reduce background or environmental noise. In this case, the microphone 310 used for audioplethysmography 110 can be implemented using a feedback microphone 330 of the active-noise-cancellation circuit 328. During active noise cancellation, the feedback microphone 330 provides feedback information regarding the performance of the active noise cancellation. During audioplethysmography 110, the feedback microphone 330 receives an acoustic signal, which is provided to the audioplethysmography measurement module 318 and/or the audioplethysmography calibration module 320. In some situations, active noise cancellation and audioplethysmography 110 are performed simultaneously using the feedback microphone 330. In this case, the acoustic signal received by the feedback microphone 330 can be provided to at least one of the audioplethysmography modules 318 or 320 and can be provided to the active-noise-cancellation circuit 328. Different types of audioplethysmography 110 are further described with respect to FIGS. 4-1 and 4-2.

Audioplethysmography

Figures 1, 4:
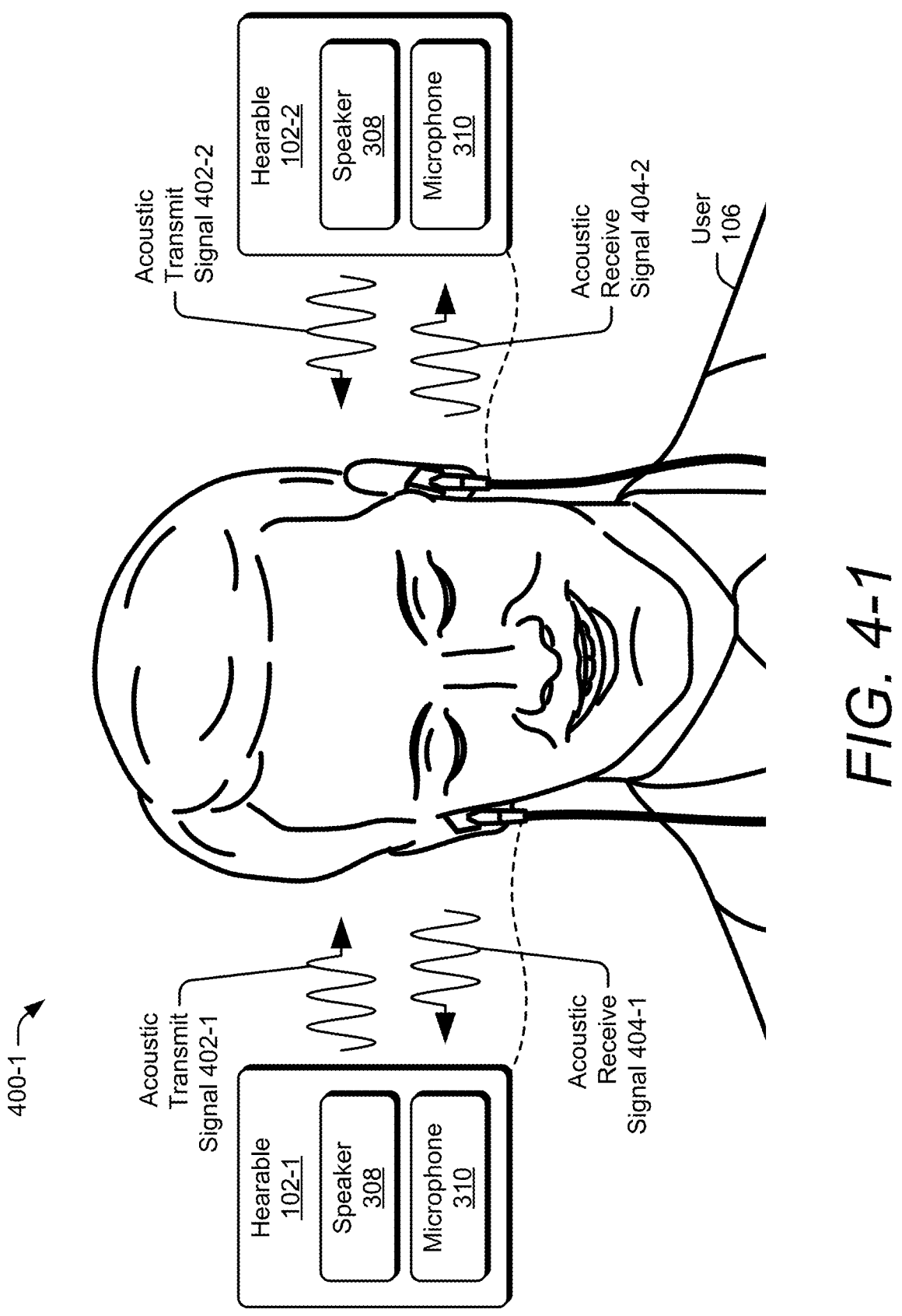
Figures 2, 4:
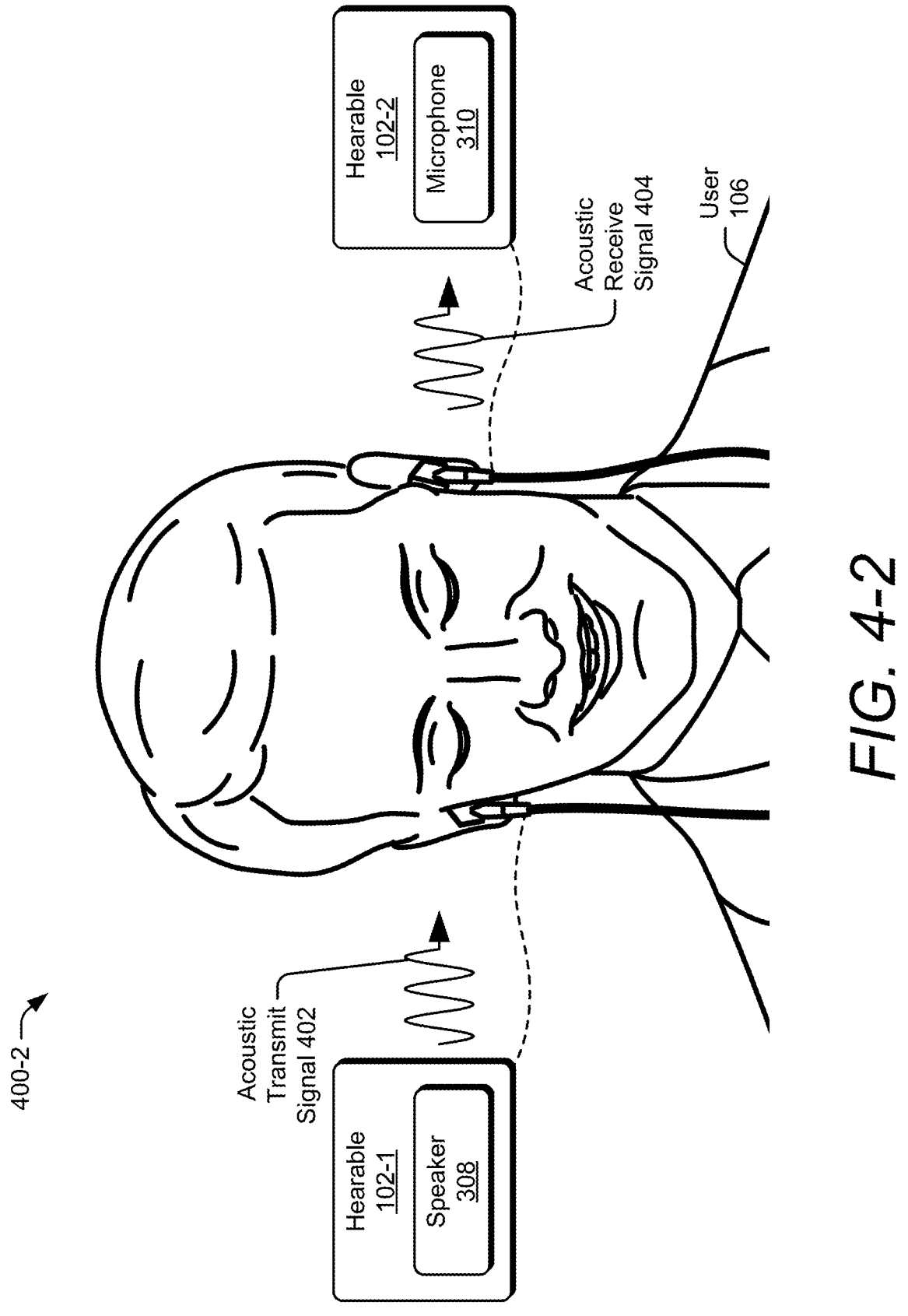

FIG. 4-1 illustrates example operations of two hearables 102-1 and 102-2 performing single-ear audioplethysmography 110. In environment 400-1, the hearables 102-1 and 102-2 independently perform audioplethysmography 110 on different ears 108 of the user 106. In this case, the first hearable 102-1 is proximate to the user 106's right ear 108, and the second hearable 102-2 is proximate to the user 106's left ear 108. Each hearable 102-1 and 102-2 includes a speaker 308 and a microphone 310. The hearables 102-1 and 102-2 can operate in a monostatic manner during the same time period or during different time periods. In other words, each hearable 102-1 and 102-2 can independently transmit and receive acoustic signals.

For example, the first hearable 102-1 uses the speaker 308 to transmit a first acoustic transmit 402-1, which propagates within at least a portion of the user 106's right ear canal 120. The first hearable 102-1 uses the microphone 310, which can be the feedback microphone 330, to receive a first acoustic receive signal 404-1. In this example, an acoustic circuit is formed that includes the seal 118, the hearable 102-1, the right ear canal 120, and the ear drum 122 of the right ear 108. The first acoustic receive signal 404-1 represents a version of the first acoustic transmit signal 402-1 that is modified, at least in part, by the acoustic circuit associated with the right ear canal 120. This modification can change an amplitude, phase, and/or frequency of the first acoustic receive signal 404-1 relative to the first acoustic transmit signal 402-1.

Similarly, the second hearable 102-2 uses the speaker 308 to transmit a second acoustic transmit signal 402-2, which propagates within at least a portion of the user 106's left ear canal 120. The second hearable 102-2 uses the microphone 310, which can be the feedback microphone 330, to receive a second acoustic receive signal 404-2. The second acoustic receive signal 404-2 represents a version of the second acoustic transmit signal 402-2 that is modified, at least in part, by the acoustic circuit associated with the left ear canal 120. This modification can change an amplitude, phase, and/or frequency of the second acoustic receive signal 404-2 relative to the second acoustic transmit signal 402-2.

In this example, the hearables 102-1 and 102-2 both operate as a transmitter and a receiver. More specifically, the hearable 102-1 represents a transmitter (or a source) of the acoustic transmit signal 402-1 and also represents a receiver (or destination) of the acoustic receive signal 404-1. Likewise, the hearable 102-2 represents a transmitter (or a source) of the acoustic transmit signal 402-2 and also represents a receiver (or destination) of the acoustic receive signal 404-2.

The techniques of single-ear audioplethysmography 110 can be particularly beneficial for biometric monitoring 112, environment sensing 116, and at least some aspects of facial behavior recognition 114. This also enables the smart device 104 to compile information from both hearables 102-1 and 102-2, which can further improve measurement confidence. For some aspects of audioplethysmography 110, it can be beneficial to analyze the acoustic channel between two ears 108, as further described with respect to FIG. 4-2.

FIG. 4-2 illustrates an example joint operation of two hearables 102-1 and 102-2 performing two-ear audioplethysmography 110. In the environment 400-2, the hearables 102-1 and 102-2 jointly perform audioplethysmography 110 across two ears 108 of the user 106. In this case, at least one of the hearables 102 (e.g., the first hearable 102-1) includes the speaker 308, and at least one of the other hearables 102 (e.g., the second hearable 102-2) includes the microphone 310. The hearables 102-1 and 102-2 operate together in a bistatic manner during the same time period.

During operation, the first hearable 102-1 transmits a first acoustic transmit 402 using the speaker 308. The acoustic transmit signal 402 propagates through the user 106's right ear canal 120. The acoustic transmit signal 402 also propagates through an acoustic channel that exists between the right and left ears 108. In the left ear 108, the acoustic transmit signal 402 propagates through the user 106's left ear canal 120 and is represented as an acoustic receive signal 404. The second hearable 102-2 receives the acoustic receive signal 404 using the microphone 310. In this example, an acoustic circuit is formed that includes the seals 118 associated with the hearables 102-1 and 102-2, the hearable 102-1, the right ear canal 120, the ear drum 122 of the right ear 108, the acoustic channel between the right and left ears 108, the ear drum 122 of the left ear 108, the left ear canal 120, and the hearable 102-2. The acoustic receive signal 404 represents a version of the acoustic transmit signal 402 that is modified by the acoustic circuit associated with the right ear canal 120, modified by the acoustic channel associated with the user 106's face, and modified by the acoustic circuit associated with the left ear canal 120. This modification can change an amplitude, phase, and/or frequency of the acoustic receive signal 404 relative to the acoustic transmit signal 402. In some cases, the hearable 102-2 measures the time-of-flight (ToF) associated with the propagation from the first hearable 102-1 to the second hearable 102-2. Sometimes a combination of single-ear and two-ear audioplethysmography 110 are applied to further improve measurement confidence. The single-ear and two-ear audioplethysmography 110 can occur during a same time period or during different time periods.

In this example, the hearable 102-1 operates as a transmitter, and the hearable 102-2 operates as a receiver. More specifically, the hearable 102-1 represents a transmitter (or a source) of the acoustic transmit signal 402. The hearable 102-2, in contrast, represents a receiver (or a destination) of the acoustic receive signal 404.

The acoustic transmit signal 402 of FIGS. 4-1 and 4-2 can represent a variety of different types of signals. As described above with respect to FIG. 3, the acoustic transmit signal 402 can be an ultrasonic signal and/or an audible signal. Also, the acoustic transmit signal 402 can be a continuous-wave signal or a pulsed signal. Some acoustic transmit signals 402 can have a particular tone or frequency. Other acoustic transmit signals 402 can have multiple tones or multiple frequencies. A variety of modulations can be applied to generate the acoustic transmit signal 402. Example modulations include linear frequency modulations, triangular frequency modulations, stepped frequency modulations, phase modulations, or amplitude modulations. The acoustic transmit signal 402 can be transmitted during an operational or mission mode, as further described with respect to FIGS. 5 and 7. Also, the acoustic transmit signal 402 can be transmitted during a calibration mode, as further described with respect to FIG. 6. An example audioplethysmography measurement module 318 is further described with respect to FIG. 5.

Figure 5:
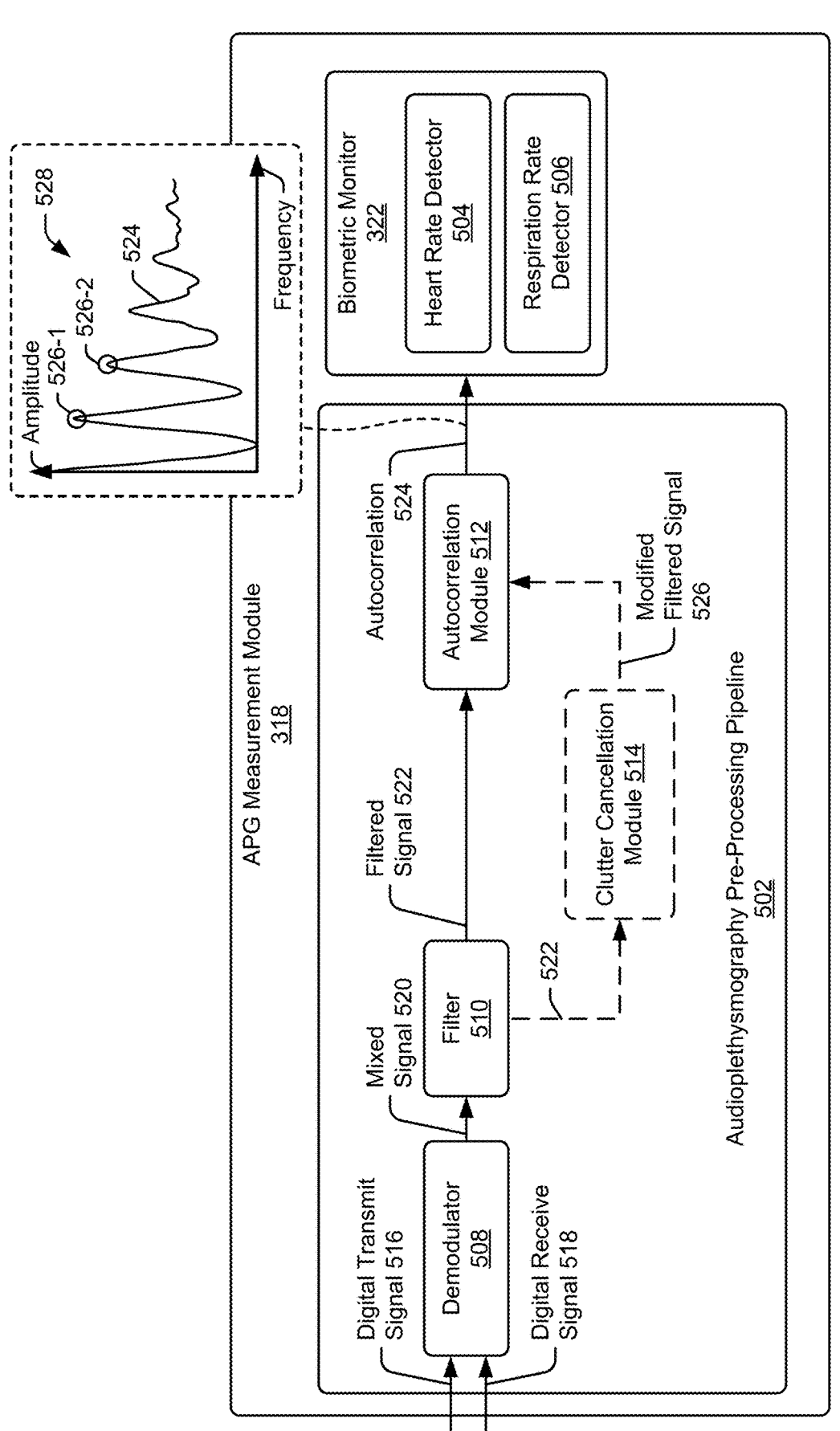
FIG. 5 illustrates an example scheme implemented by an audioplethysmography measurement module of a hearable.

FIG. 5 illustrates an example scheme implemented by the audioplethysmography measurement module 318. In the depicted configuration, the audioplethysmography measurement module 318 includes at least one audioplethysmography pre-processing pipeline 502 and at least one biometric monitor 322. The audioplethysmography pre-processing pipeline 502 processes digital samples of the acoustic receive signal 404 and outputs data in a format that is usable by the biometric monitor 322. The biometric monitor 322 determines one or more physiological metrics (e.g., one or more biometrics) of the user 106 for biometric monitoring 112. In this example, the biometric monitor 322 includes a heart rate detector 504 and/or a respiration rate detector 506. The heart rate detector 504 measures a heart rate of the user 106. The respiration rate detector 506 measures a respiration rate of the user 106.

Other implementations are also possible in which the audioplethysmography measurement module 318 includes the facial behavior detector 324 and/or the environment detector 326 coupled to an output of the audioplethysmography pre-processing pipeline 502. In general, the audioplethysmography measurement module 318 can include any combination of the biometric monitor 322, the facial behavior detector 324 and/or the environment detector 326.

The audioplethysmography pre-processing pipeline 502 includes at least one demodulator 508, at least one filter 510, and at least one autocorrelation module 512. The demodulator 508 can operate as a mixer and perform a multiplication operation. The filter 510, which can be implemented as a low-pass filter, is designed to attenuate spurious or undesired frequencies. Example spurious frequencies include harmonic frequencies generated through operation of the demodulator 508. The audioplethysmography pre-processing pipeline 502 can optionally include a clutter cancellation module 514. The clutter cancellation module 514 can attenuate other undesired frequencies that are passed by the filter 510.

During audioplethysmography 110, the audioplethysmography pre-processing pipeline 502 accepts a digital transmit signal 516, which represents a version of the acoustic transmit signal 402. In some implementations, the system processor 314 generates the digital transmit signal 516 in the digital domain and passes the digital transmit signal 516 to the analog circuit 312 to enable transmission of the acoustic transmit signal 402 via the transducer 306. The audioplethysmography pre-processing pipeline 502 also accepts a digital receive signal 518 from the analog circuit 312. The digital receive signal 518 represents a digital version of the acoustic receive signal 404.

Using the digital transmit signal 516, the demodulator 508 demodulates the digital receive signal 518 to generate a mixed signal 520. As an example, the demodulator 508 can multiply or perform a beating operation to combine the digital transmit signal 516 with the digital receive signal 518. For example, the demodulator 508 may apply an In-phase and Quadrature (IQ) mixing for the digital receive signal 518 using the digital transmit signal 516. Referring to Equation 2 above, an in-phase digital transmit signal 516 may be given by $S_f(t)=\cos(\Omega_{f_C}(t))$ and the demodulator 508 may then perform a multiplication of S(t) and $S_f(t)$. The filter 510 filters the mixed signal 520 to generate a filtered signal 522. Due to the operation of the filter 510, some higher-frequency components of the filtered signal 522 can be attenuated relative to the mixed signal 520. Based on filtering, for example when applying an IQ mixing for the digital receive signal 518, an in-phase part I(t) and a quadrature-phase part Q(t) may be determined as well as an amplitude $R(t)=\sqrt{I(t)^2+Q(t)^2}$ or a phase $$\Phi(t) = \arctan\frac{Q(t)}{I(r)}$$

of the digital receive signal 518.

In a first example implementation, the autocorrelation module 512 accepts the filtered signal 522 and applies an autocorrelation function to generate autocorrelation 524. The biometric monitor 322 analyzes the autocorrelation 524 to measure a physiological metric of the user 106. For example, the heart rate detector 504 detects peaks 526 of the autocorrelation 524 and measures the time interval between the peaks 526. This time interval, or period of the autocorrelation 524, represents the heart rate. At 528, a graph of an example autocorrelation 524 is shown having peaks 526-1 and 526-2, which can be used to determine the heart rate. A similar process can occur for measuring the respiration rate using the respiration rate detector 506.

Sometimes frequencies associated with other physiological metrics or noise can make it harder to accurately measure the desired physiological metric. To address this, the audioplethysmography pre-processing pipeline 502 can apply the clutter cancellation module 514. Instead of directly sending the filtered signal 522 to the autocorrelation module 512, the clutter cancellation module 514 operates on the filtered signal 522 and generates a modified filtered signal 526. For example, the clutter cancellation module 514 can attenuate frequencies that are outside of a range associated with the heart rate. These can include slower frequencies associated with a respiration rate of the user 106 and/or frequencies associated with movement of the hearable 102.

In an example implementation, the clutter cancellation module 514 applies a curve fitting (e.g., a fifth-order polynomial curve fit) onto the filtered signal 522 to generate a fitted curve. The fitted curve has a frequency that incorporates, at least in part, the frequency associated with noise or other physiological metrics that are not of interest. The clutter cancellation module 514 then subtracts the fitted curve from the filtered signal 522 to generate the modified filtered signal 526. The modified filtered signal 526 is passed to the autocorrelation module 512 and the measurement process can continue as described above.

Some transmission frequencies can be better for audioplethysmography 110 than others. The desired frequency can depend, at least in part, on the quality of the seal 118 and the physical structure of the ear canal 120. To determine the desired frequency, the hearable 102 can optionally perform a calibration process using the audioplethysmography calibration module 320, which is further described with respect to FIG. 6.

Figure 6:
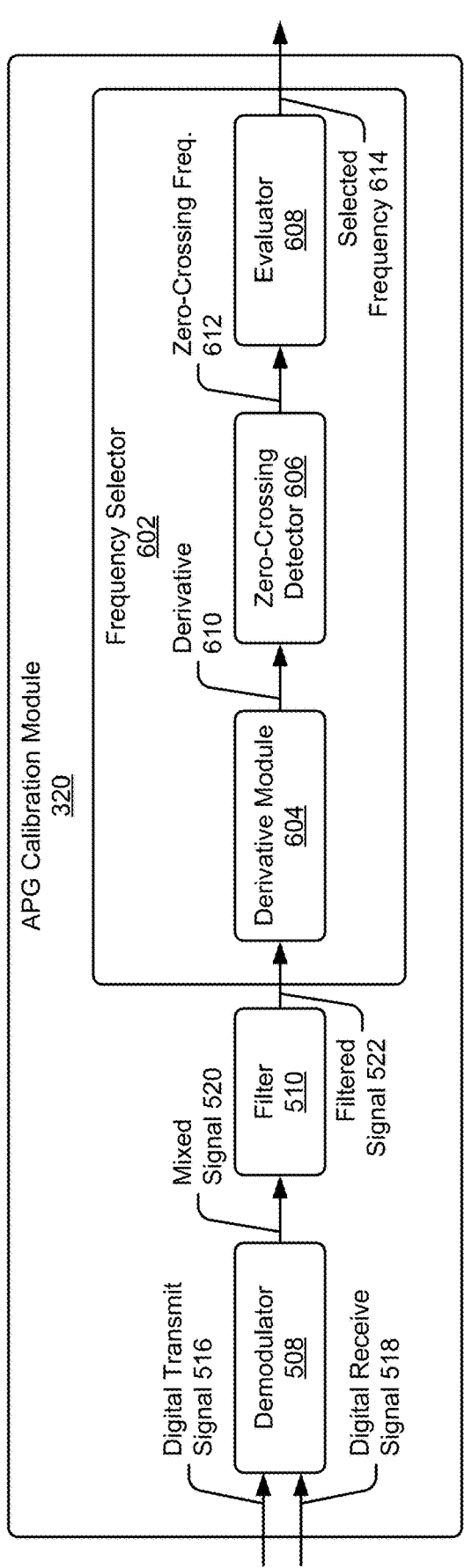
FIG. 6 illustrates an example scheme implemented by an audioplethysmography calibration module of a hearable.

FIG. 6 illustrates an example scheme implemented by the audioplethysmography calibration module 320. In the depicted configuration, the audioplethysmography calibration module 320 includes the demodulator 508, the filter 510, and at least one frequency selector 602. The frequency selector 602 one selects or more acoustic frequencies for audioplethysmography 110. In an example implementation, the frequency selector 602 includes a derivative module 604, a zero-crossing detector 606, and an evaluator 608. The operations of these components are further described below.

During a calibration mode, the hearable 102 transmits the acoustic transmit signal 402 and receives the acoustic receive signal 404. The acoustic transmit signal 402 can have a particular bandwidth on the order of several kilohertz. For example, the acoustic transmit signal 402 can have a bandwidth of approximately 4, 6, 8, 10, 16, or 20 kilohertz. The audioplethysmography calibration module 320 accepts the digital transmit signal 516, which represents a version of the acoustic transmit signal 402. Also, the audioplethysmography calibration module 320 accepts the digital receive signal 518, which represents a digital version of the acoustic receive signal 404.

Using the digital transmit signal 516, the demodulator 508 demodulates the digital receive signal 518 to generate the mixed signal 520, as described above with respect to FIG. 5. The filter 510 filters the mixed signal 520 to attenuate spurious or undesired frequencies and to generate the filtered signal 522.

The derivative module 604 calculates a second-order derivative of the frequency response of the filtered signal 522 to generate derivative 610. The zero-crossing detector 606 identifies frequencies within the derivative 610 that are associated with zero crossings. These zero-crossing frequencies 612 represent frequencies that are particularly sensitive to changes in the acoustic channel or the acoustic circuit. The zero-crossing frequencies 612 are passed to the evaluator 608.

The evaluator 608 identifies one or more zero-crossing frequencies 612 for audioplethysmography 110, which are represented by selected frequency 614. To determine the selected frequency 614, the evaluator 608 can take into account the difference between adjacent zero-crossing frequencies 612 and/or an amount of energy within the filtered signal 522 at the zero-crossing frequencies 612. In general, the evaluator 608 selects frequencies that are sufficiently far apart to reduce interference and have a sufficient amount of energy to perform audioplethysmography 110. The resulting selected frequency 614 (or selected frequencies 614) can be used to achieve accurate results for audioplethysmography 110. As an example, the evaluator 608 can select 1, 2, 3, 4, 6 or 10 different frequencies.

In some cases, the evaluator 608 can apply an autocorrelation function to evaluate the performance of each selected frequency 614. Selected frequencies 614 that produce an autocorrelation function having a peak-to-average ratio that is greater than a predetermined threshold can be candidates for selection.

The hearable 102 can use at least one of the selected frequencies 614 to transmit subsequent acoustic transmit signals 402 for audioplethysmography 110. This calibration process can be performed as often as desired to account for changes in the seal 118 and/or changes in the physical structure of the ear canal 120. In some implementations, the hearable 102 detects the formation of the seal 118 and performs the calibration process based on this detection. The hearable 102 can detect the formation of the seal 118 using audioplethysmography 110 or using another sensor that performs on-head (or in-ear) detection. Also, the calibration process can be performed for each ear 108. In some cases, the hearable 102 uses multiple selected frequencies 614 to transmit a subsequent acoustic transmit signal 402. In this case, the audioplethysmography measurement module 318 can execute multiple audioplethysmography pre-processing pipelines 502, as further described with respect to FIG. 7.

Figure 7:
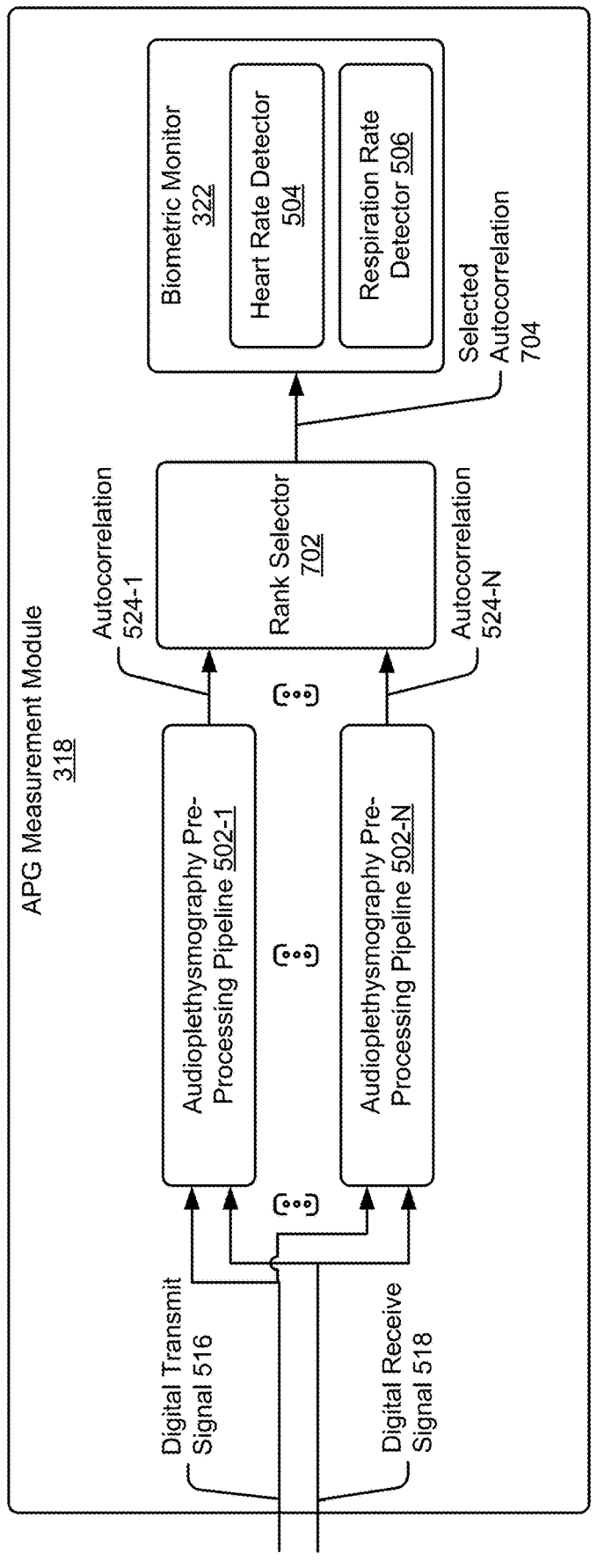
FIG. 7 illustrates another example scheme implemented by an audioplethysmography measurement module of a hearable.

FIG. 7 illustrates another example scheme implemented by the audioplethysmography measurement module 318. In this case, the hearable 102 transmits an acoustic transmit signal 402 with multiple tones or frequencies, which can be based on the selected frequencies 614 determined during a calibration mode. As shown in FIG. 7, the audioplethysmography measurement module 318 includes multiple audioplethysmography pre-processing pipelines 502-1 to 502-N. Each audioplethysmography pre-processing pipelines 502-1 to 502-N is designed to process information associated with one of the selected frequencies 614 and generate a corresponding autocorrelation 524-1 to 524-N.

The audioplethysmography measurement module 318 also includes a rank selector 702, which evaluates the autocorrelations 524-1 to 524-N and selects the autocorrelation with the highest quality factor. For example, the rank selector 702 can select one of the autocorrelations 524-1 to 524-N with a highest peak-to-average ratio in the frequency domain of the autocorrelation. This selected autocorrelation 704 is passed to other modules, such as the biometric monitor 322, the facial behavior detector 324, or the environment detector 326, for further processing. This selection process enables the audioplethysmography measurement module 318 to achieve a higher level of accuracy for performing audioplethysmography 110, including for measuring at least one physiological metric as part of biometric monitoring 112. FIGS. 8 to 11 further graphically illustrate example signals associated with a calibration process implemented by an audioplethysmography calibration module 320 and as explained with respect to FIG. 6.

Figure 8:
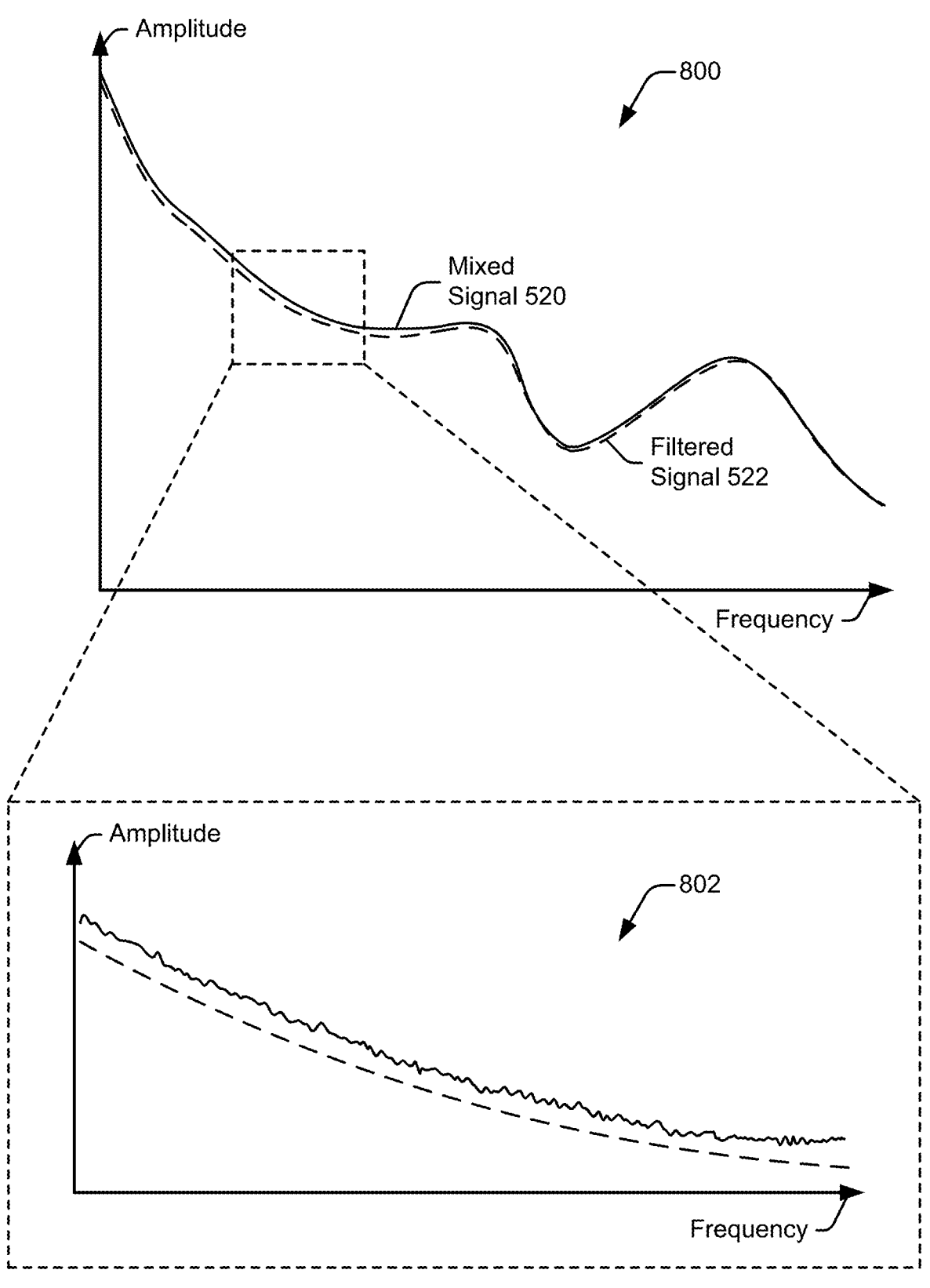
FIG. 8 illustrates graphs of an example mixed signal and an example filtered signal in a calibration phase.

FIG. 8 illustrates graphs 800 and 802 of an example mixed signal 520 and an example filtered signal 522. The graphs 800 and 802 depict amplitude over frequency. The graph 802 represents an enlarged view of a section of the graph 800. As shown in 802, the mixed signal 520 has at least some noise. The filtered signal 522 represents a smoother version of the mixed signal 520.

Figure 9:
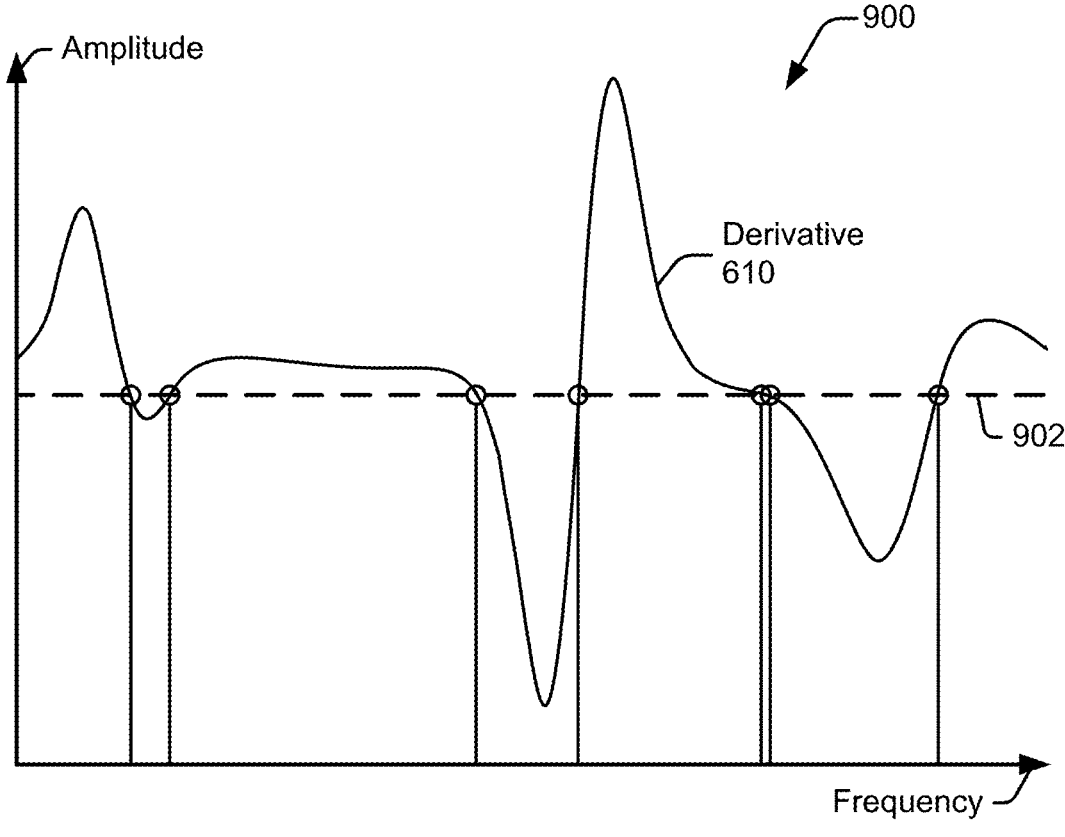
FIG. 9 illustrates a graph of an example derivative of a filtered signal generated in a calibration phase.

FIG. 9 illustrates a graph 900 of an example derivative 610 of the filtered signal 522 of FIG. 8. In this example, the derivative 610 represents a second-order derivative as calculated by the derivative module 604. Dashed line 902 represents a zero amplitude. The zero-crossing detector 606 calculates and identifies frequencies at which the derivative 610 crosses the zero amplitude represented by 902. Based on these zero-crossings, several frequencies are identified. These frequencies can be particularly sensitive to changes in the acoustic channel or the acoustic circuit. The frequencies are further described with respect to FIG. 10.

Figure 10:
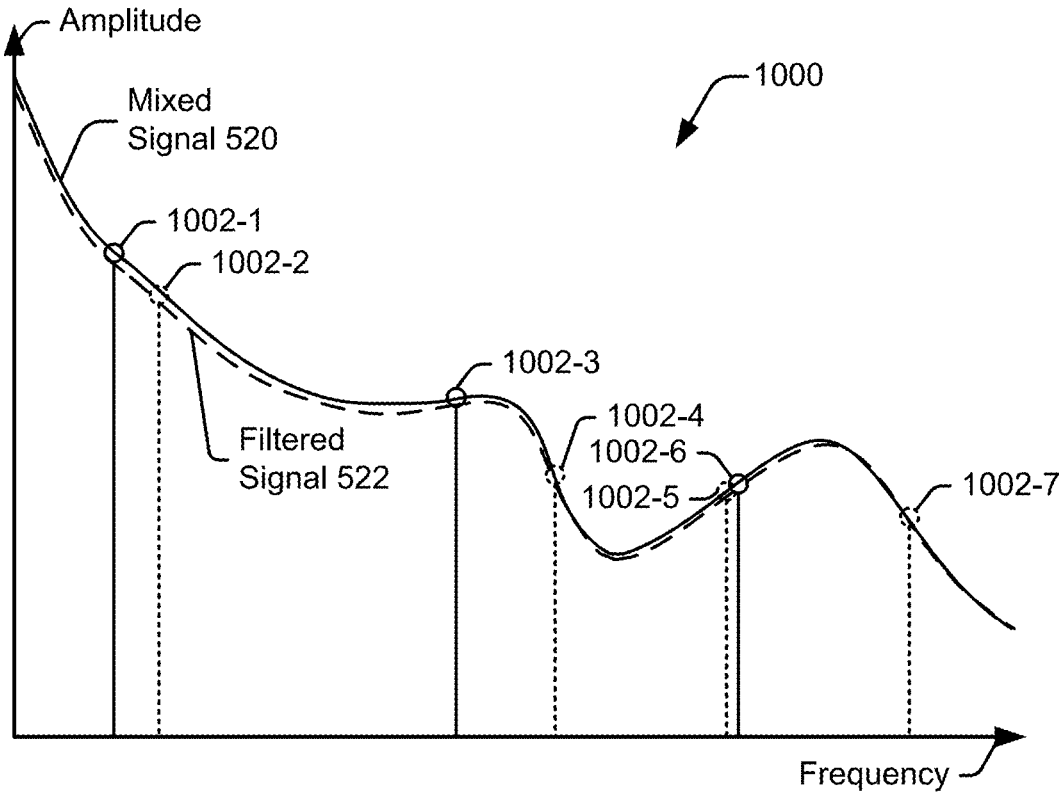
FIG. 10 illustrates a graph showing a relationship between zero-crossing frequencies associated with a derivative and amplitudes of example mixed and filtered signals in a calibration phase.

FIG. 10 illustrates a graph 1000 in which frequencies 1002-1 to 1002-7 associated with the zero-crossings of FIG. 9 are shown relative to the mixed signal 520 and the filtered signal 522 of FIG. 8. The evaluator 608 evaluates the zero-crossing frequencies 1002-1 to 1002-7 and (pre-) selects a subset of the frequencies 1002 taking into account the difference between the adjacent zero-crossing frequencies and/or an amount of energy within the filtered signal 522 at a zero-crossing frequency 1002. This may result in the (pre-) selecting of frequencies 1002-1, 1002-3, 1002-6, which are shown by solid lines, and may result in the not selecting of frequencies 1002-2, 1002-4, 1002-5, and 1002-7, which are shown by dashed lines. This operation can result in the (pre-) selecting of different frequencies for each ear 108, including, for example, zero-crossing frequencies 1002 having a highest amplitude. The autocorrelation 524 applied by the evaluator 608 for evaluating performance of each one of the selected frequencies 1002 with respect to audioplethysmography 110 is further described with respect to FIG. 11.

Figure 11:
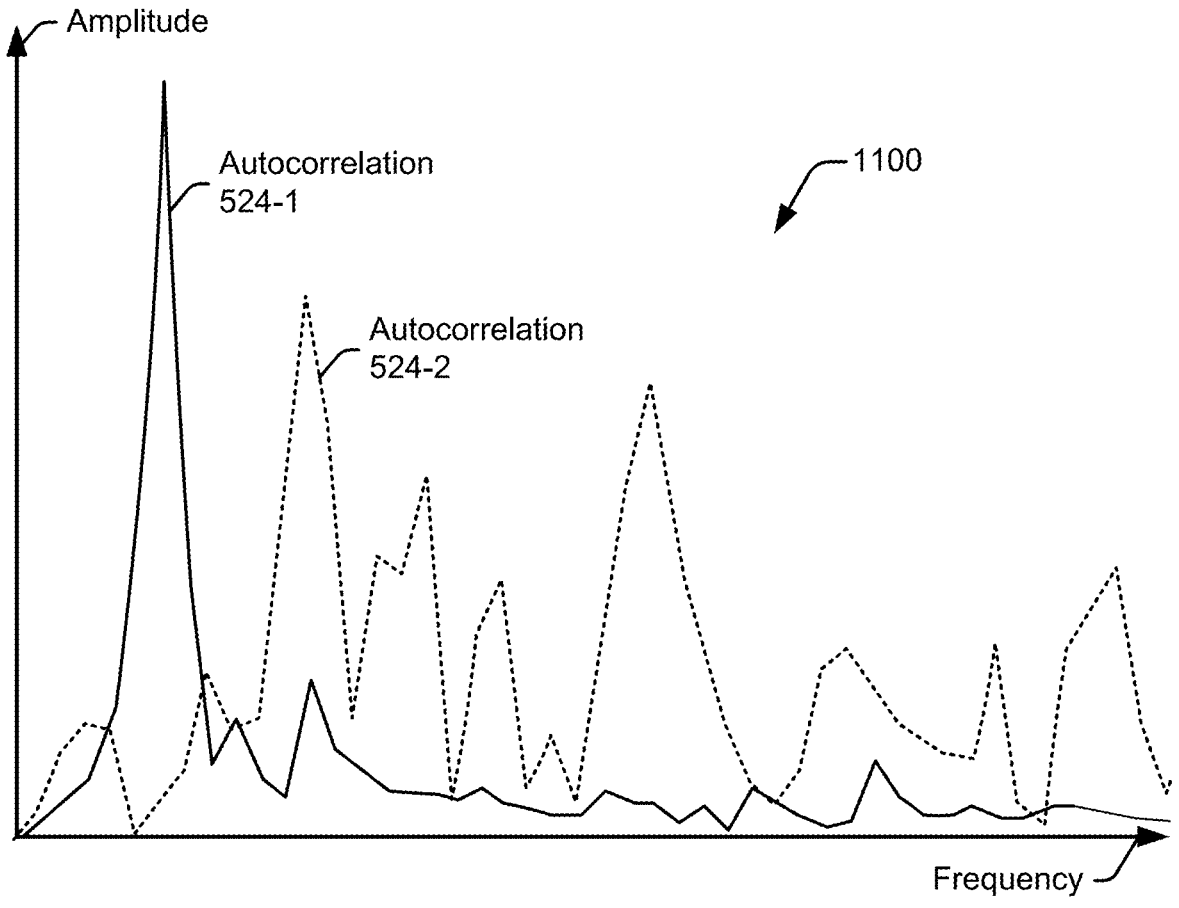
FIG. 11 illustrates a graph that depicts example autocorrelations.

FIG. 11 illustrates a graph 1100 that depicts example autocorrelations 524-1 and 524-2. The autocorrelations 524-1 and 524-2 can be associated with different ones of the frequencies 1002 shown in FIG. 10. As can be seen from the corresponding plots of 524-1 and 524-2, the calculated autocorrelations 524-1 and 524-2 may indicate that with a (pre-) selected frequency a physiological metric, such as a heart rate of the user 106, may not be determined. Accordingly, the evaluator 608, will (finally) select frequencies 1002 that generate an autocorrelation 524 with a peak-to-average ratio that is greater than a predetermined threshold in order to determine the frequencies 1002 to be used for the audioplethysmography 110. In this context, the autocorrelation 524-1 can have a sufficiently high peak-to-average ratio, which causes its associated frequency 1002 to be selected. The autocorrelation 524-2, however, has a peak-to-average ratio that is too low and causes its associated frequency 1002 to not be selected.

Example Methods

Figure 14:
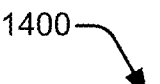
FIG. 14 illustrates a third example method for performing an aspect of audioplethysmography.

FIGS. 12 to 14 depict example methods 1200, 1300, and 1400 for implementing aspects of audioplethysmography 110. Methods 1200, 1300, and 1400 are shown as sets of operations (or acts) performed but not necessarily limited to the order or combinations in which the operations are shown herein. Further, any of one or more of the operations may be repeated, combined, reorganized, or linked to provide a wide array of additional and/or alternate methods. In portions of the following discussion, reference may be made to the environment 100 of FIG. 1, and entities detailed in FIGS. 2 and 3, reference to which is made for example only. The techniques are not limited to performance by one entity or multiple entities operating on one device.

At 1202 in FIG. 12, an acoustic transmit signal is transmitted. The acoustic transmit signal propagates within at least a portion of an ear canal of a user. For example, at least one speaker 308 transmits the acoustic transmit signal 402. The at least one speaker 308 can represent the speaker of the hearable 102-1, the speaker of the hearable 102-2, or both.

The acoustic transmit signal 402 propagates within at least a portion of the ear canal 120 of the user 106, as described with respect to FIG. 4-1 or 4-2.

At 1204, an acoustic receive signal is received. The acoustic receive signal represents a version of the acoustic transmit signal with one or more waveform characteristics modified due to the propagation within the ear canal. For example, at least one microphone 310 receives the acoustic receive signal 404, as described with respect to FIG. 4-1 or 4-2. The at least one microphone 310 can represent the microphone 310 of the hearable 102-1, the microphone of the hearable 102-2, or both. The acoustic receive signal 404 represents a version of the acoustic transmit signal 402 with one or more waveform characteristics modified due to the propagation within the ear canal 120. The waveform characteristics can also be modified, at least in part, by the user's biometrics, by the user's facial behavior, or by the environment around the ear canal 120. Example waveform characteristics include amplitude, phase, and/or frequency. In some implementations, a feedback microphone 330 of an active-noise-cancellation circuit 328 can receive the acoustic receive signal 404.

At 1206, at least one physiological metric of the user is determined based on the one or more modified waveform characteristics of the acoustic receive signal. For example, the hearable 102 determines at least one physiological metric of the user 106 in accordance with biometric monitoring 112. Example physiological metrics include a heart rate, a respiration rate, blood pressure, body temperature, and a carbon dioxide level.

At 1302 in FIG. 13, an acoustic transmit signal is transmitted. The acoustic transmit signal propagates within at least a portion of an ear canal of a user. For example, at least one speaker 308 transmits the acoustic transmit signal 402. The at least one speaker 308 can represent the speaker of the hearable 102-1, the speaker of the hearable 102-2, or both. The acoustic transmit signal 402 propagates within at least a portion of the ear canal 120 of the user 106, as described with respect to FIGS. 4-1 and 4-2.

At 1304, an acoustic receive signal is received. The acoustic receive signal represents a version of the acoustic transmit signal with one or more waveform characteristics modified due to the propagation within the ear canal. For example, at least one microphone 310 receives the acoustic receive signal 404, as described with respect to FIG. 4-1 or 4-2. The at least one microphone 310 can represent the microphone 310 of the hearable 102-1, the microphone 310 of the hearable 102-2, or both. The acoustic receive signal 404 represents a version of the acoustic transmit signal 402 with one or more waveform characteristics modified due to the propagation within the ear canal 120. As the user 106 breathes, the gas composition within the ear canal 120 changes, as shown in FIG. 1-3. In particular, the carbon dioxide concentration changes, which impacts the speed of sound within the ear canal 120. Example waveform characteristics can include amplitude, phase, and/or frequency. In some implementations, a feedback microphone 330 of an active-noise-cancellation circuit 328 can receive the acoustic receive signal 404.

At 1306, a respiration rate of the user is determined by analyzing the one or more waveform characteristics of the acoustic receive signal. For example, the hearable 102 determines the respiration rate based on the one or more waveform characteristics of the acoustic receive signal 404 using the audioplethysmography measurement module 318 and the respiration rate detector 506, as described with respect to FIG. 5.

Optionally at 1308, the respiration rate is communicated to a smart device to enable the smart device to display the respiration rate to the user. For example, the hearable 102 communicates the respiration rate to the smart device 104 to enable the smart device 104 to communicate (e.g., display) the respiration rate to the user 106.

At 1402 in FIG. 14, a calibration process is performed that identifies at least one acoustic frequency suitable for audioplethysmography using at least one speaker and at least one microphone. For example, the hearable 102 uses at least one speaker 308, at least one microphone 310 and the audioplethysmography calibration module 320 to perform a calibration process that identifies at least one acoustic frequency that is suitable for audioplethysmography 110, as described with respect to FIG. 6.

At 1404, audioplethysmography is performed using the at least one acoustic frequency at an ear of a user. For example, the hearable 102 performs audioplethysmography 110 using the selected frequency 614. In particular, the hearable 102 uses the at least one acoustic frequency (e.g., transmits an acoustic transmit signal 402 using the selected frequency 614) to perform audioplethysmography at an ear 108 (e.g., at one or more ears 108) of a user 106. The hearable 102 analyzes a received acoustic receive signal 404 using the audioplethysmography measurement module 318.

In some situations, the methods 1200, 1300, and/or 1400 are performed using one hearable 102 for single-ear audioplethysmography 110, as described with respect to FIG. 4-1. In other situations, the methods 1200, 1300, and/or 1400 are performed using two hearables 102 for two-ear audioplethysmography 110, as described with respect to FIG. 4-2.

Example Computing System

Figure 15:
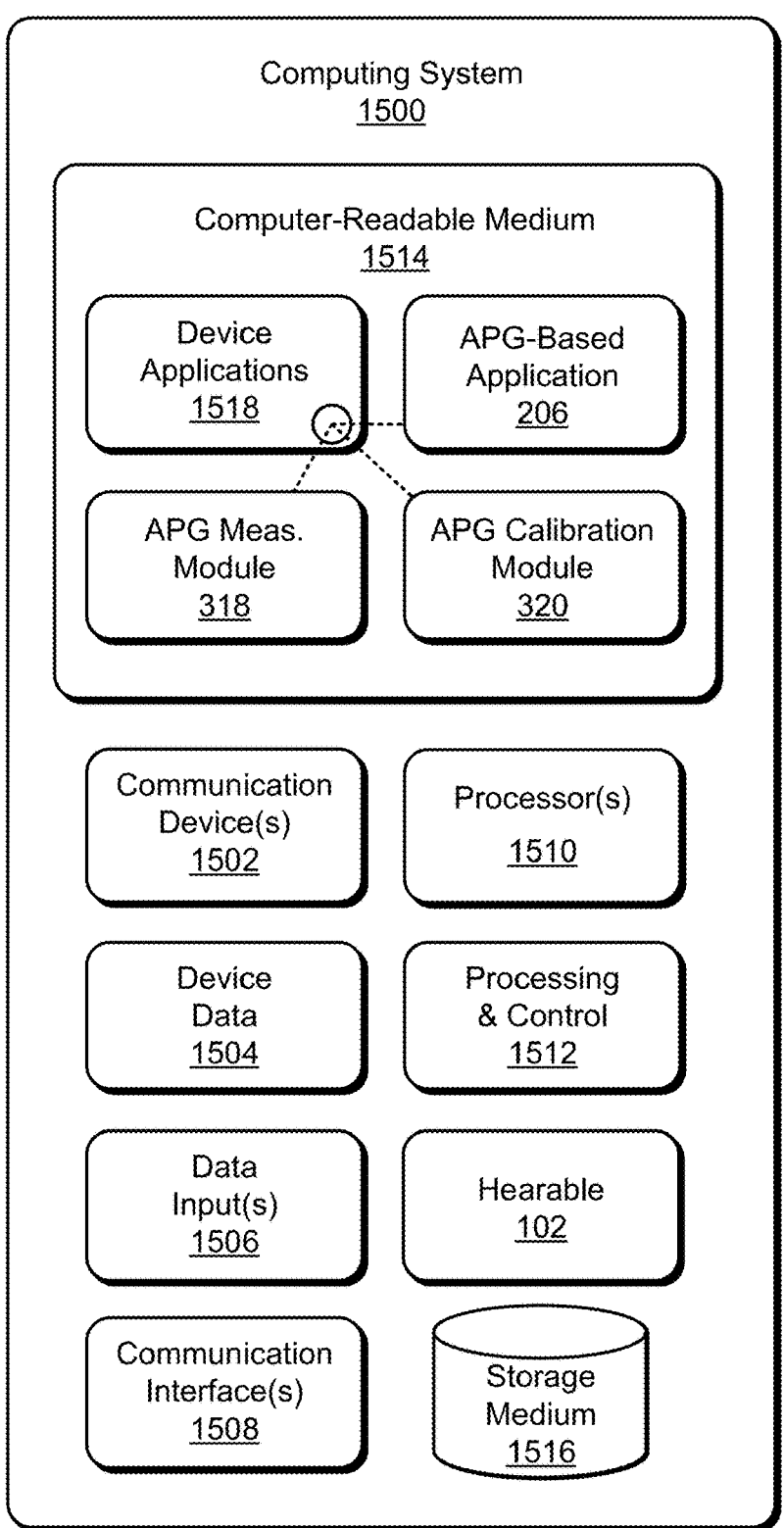
FIG. 15 illustrates an example computing system embodying, or in which techniques may be implemented that enable use of, audioplethysmography.

FIG. 15 illustrates various components of an example computing system 1500 that can be implemented as any type of client, server, and/or computing device as described with reference to the previous FIGS. 2 and 3 to implement aspects of audioplethysmography calibration.

The computing system 1500 includes communication devices 1502 that enable wired and/or wireless communication of device data 1504 (e.g., received data, data that is being received, data scheduled for broadcast, or data packets of the data). The communication devices 1502 or the computing system 1500 can include one or more hearables 102. The device data 1504 or other device content can include configuration settings of the device, media content stored on the device, and/or information associated with a user of the device. Media content stored on the computing system 1500 can include any type of audio, video, and/or image data. The computing system 1500 includes one or more data inputs 1506 via which any type of data, media content, and/or inputs can be received, such as human utterances, user-selectable inputs (explicit or implicit), messages, music, television media content, recorded video content, and any other type of audio, video, and/or image data received from any content and/or data source.

The computing system 1500 also includes communication interfaces 1508, which can be implemented as any one or more of a serial and/or parallel interface, a wireless interface, any type of network interface, a modem, and as any other type of communication interface. The communication interfaces 1508 provide a connection and/or communication links between the computing system 1500 and a communication network by which other electronic, computing, and communication devices communicate data with the computing system 1500.

The computing system 1500 includes one or more processors 1510 (e.g., any of microprocessors, controllers, and the like), which process various computer-executable instructions to control the operation of the computing system 1500. Alternatively or in addition, the computing system 1500 can be implemented with any one or combination of hardware, firmware, or fixed logic circuitry that is implemented in connection with processing and control circuits which are generally identified at 1512. Although not shown, the computing system 1500 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

The computing system 1500 also includes a computer-readable medium 1514, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. The disk storage device may be implemented as any type of magnetic or optical storage device, such as a hard disk drive, a recordable and/or rewriteable compact disc (CD), any type of a digital versatile disc (DVD), and the like. The computing system 1500 can also include a mass storage medium device (storage medium) 1516.

The computer-readable medium 1514 provides data storage mechanisms to store the device data 1504, as well as various device applications 1518 and any other types of information and/or data related to operational aspects of the computing system 1500. For example, an operating system 1520 can be maintained as a computer application with the computer-readable medium 1514 and executed on the processors 1510. The device applications 1518 may include a device manager, such as any form of a control application, software application, signal-processing and control module, code that is native to a particular device, a hardware abstraction layer for a particular device, and so on.

The device applications 1518 also include any system components, engines, or managers to implement audioplethysmography 110. In this example, the device applications 1518 include the audioplethysmography-based application 206 (APG-based application 206) of FIG. 2, the audioplethysmography measurement module 318 of FIG. 3, and optionally the audioplethysmography calibration module 320 of FIG. 3.

Some examples are described below.

Example 1: A method comprising:

performing a calibration process that identifies at least one acoustic frequency suitable for audioplethysmography using at least one speaker and at least one microphone; and using the at least one acoustic frequency for performing the audioplethysmography at an ear of a user.

Example 2: The method of example 1, further comprising:

detecting whether an ear canal of the user is at least partially sealed by a device comprising the at least one speaker and/or the at least one microphone; and responsive to the detecting, initiating the performing of the calibration process.

Example 3: The method of example 1 or 2, wherein:

the performing of the calibration process comprises performing a first calibration process at a first ear using a first speaker of the at least one speaker and a first microphone of the at least one microphone;

the using the at least one acoustic frequency comprises using the at least one acoustic frequency for performing the audioplethysmography at the first ear; and the method further comprises:

performing, at a second ear of the user, a second calibration process that identifies at least one second acoustic frequency suitable for the audioplethysmography using a second speaker of the at least one speaker and a second microphone of the at least one microphone; and using the at least one second acoustic frequency for performing the audioplethysmography at the second ear.

Example 4: The method of any one of the preceding examples, further comprising:

transmitting audible content during at least a portion of time that the calibration process is performed or during at least a portion of time that the audioplethysmography is performed.

Example 5: The method of any one of the preceding examples, wherein the performing of the calibration process comprises:

transmitting a first acoustic transmit signal having multiple frequencies, the first acoustic transmit signal propagating within at least a portion of an ear canal of the user;

receiving a first acoustic receive signal, the first acoustic receive signal representing a version of the first acoustic transmit signal that has one or more waveform characteristics modified based on the propagation within the ear canal; and selecting the at least one acoustic frequency from the multiple frequencies based on the one or more waveform characteristics.

Example 6: The method of example 5, wherein the selecting the at least one acoustic frequency comprises:

demodulating the first acoustic receive signal by mixing a digital version of the first acoustic receive signal with a digital version of the first acoustic transmit signal to generate a first mixed signal;

passing the first mixed signal through a low-pass filter to generate a first filtered signal;

determining a second derivative of the first filtered signal;

identifying zero-crossing frequencies associated with the second derivative of the first filtered signal; and selecting the at least one acoustic frequency from the zero-crossing frequencies.

Example 7: The method of example 5 or 6, wherein the transmitting of the first acoustic transmit signal comprises transmitting the first acoustic transmit signal having a bandwidth of at least four kilohertz.

Example 8: The method of any one of examples 5-7, wherein the first acoustic transmit signal comprises at least one of the following:

an ultrasound signal having frequencies between approximately twenty kilohertz and two megahertz; or an audible signal having frequencies between approximately twenty hertz and twenty kilohertz.

Example 9: The method of any one of the preceding examples, wherein:

the using the at least one acoustic frequency comprises transmitting a second acoustic transmit signal having the at least one acoustic frequency, the second acoustic transmit signal propagating within at least a portion of an ear canal of the user; and the method further comprises:

receiving a second acoustic receive signal, the second acoustic receive signal representing a version of the second acoustic transmit signal that has one or more waveform characteristics modified based on the propagation within the ear canal; and determining at least one physiological metric of the user based on the one or more modified waveform characteristics of the second acoustic receive signal.

Example 10: The method of example 9, wherein the determining of the at least one physiological metric of the user comprises:

demodulating the second acoustic receive signal by mixing a digital version of the second acoustic receive signal with a digital version of the second acoustic transmit signal to generate a second mixed signal;

passing the second mixed signal through a low-pass filter to generate a second filtered signal;

generating an autocorrelation of the second filtered signal; and determining a period of the autocorrelation of the second filtered signal to determine the at least one physiological metric.

Example 11: The method of example 9 or 10, wherein the at least one physiological metric comprises at least one of the following:

a heart rate of the user; or a respiration rate of the user.

Example 12: A device comprising:

at least one speaker;

at least one microphone; and at least one processor, the device configured to perform, using the at least one speaker, the at least one microphone, and the at least one processor, any one of the methods of examples 1-11.

Example 13: The device of example 12, further comprising:

an active-noise-cancellation circuit comprising the at least one microphone.

Example 14: The device of example 13, wherein the at least one speaker and the at least one microphone are configured to be positioned proximate to one ear of a user.

Example 15: The device of example 12, wherein:

the at least one speaker is configured to be positioned proximate to a first ear of a user; and the at least one microphone is configured to be positioned proximate to a second ear.

Example 16: The device of any one of examples 12-15, wherein the at least one speaker and/or the least one microphone is part of at least one transducer of the device.

Example 17: The device of any one of examples 12-16, wherein the device is configured to at least partially seal one or more ears of a user.

Example 18: The device of any one of examples 12-17, wherein the device comprises:

at least one earbud; or headphones.

CONCLUSION

Although techniques using, and apparatuses including, facilitating audioplethysmography calibration have been described in language specific to features and/or methods, it is to be understood that the subject of the appended claims is not necessarily limited to the specific features or methods described. Rather, the specific features and methods are disclosed as example implementations of facilitating audioplethysmography calibration.

What is claimed is:

1. A method comprising:

performing a calibration process that identifies, from a set of multiple frequencies, at least one acoustic frequency suitable for audioplethysmography using at least one speaker and at least one microphone, the performing of the calibration process comprising:

transmitting a first acoustic transmit signal having the set of multiple frequencies, the first acoustic transmit signal propagating within at least a portion of an ear canal of a user;

receiving a first acoustic receive signal, the first acoustic receive signal representing a version of the first acoustic transmit signal that has one or more waveform characteristics modified based on the propagation within the ear canal; and selecting the at least one acoustic frequency from the set of multiple frequencies based on the one or more waveform characteristics; and performing, using the at least one acoustic frequency selected by the calibration process, the audioplethysmography at an ear of the user.

2. The method of claim 1, further comprising:

detecting whether an ear canal of the user is at least partially sealed by a device comprising the at least one speaker and/or the at least one microphone; and responsive to the detecting, initiating the performing of the calibration process.

3. The method of claim 1, wherein:

the performing of the calibration process comprises performing a first calibration process at a first ear using a first speaker of the at least one speaker and a first microphone of the at least one microphone;

the using the at least one acoustic frequency comprises using the at least one acoustic frequency for performing the audioplethysmography at the first ear; and the method further comprises:

performing, at a second ear of the user, a second calibration process that identifies at least one second acoustic frequency suitable for the audioplethysmography using a second speaker of the at least one speaker and a second microphone of the at least one microphone; and using the at least one second acoustic frequency for performing the audioplethysmography at the second ear.

4. The method of claim 1, further comprising:

transmitting audible content during at least a portion of time that the calibration process is performed or during at least a portion of time that the audioplethysmography is performed.

5. The method of claim 1, wherein the at least one frequency comprises two or more frequencies from the set of multiple frequencies.

6. The method of claim 1, wherein the selecting the at least one acoustic frequency comprises:

demodulating the first acoustic receive signal by mixing a digital version of the first acoustic receive signal with a digital version of the first acoustic transmit signal to generate a first mixed signal;

passing the first mixed signal through a low-pass filter to generate a first filtered signal;

determining a second derivative of the first filtered signal;

identifying zero-crossing frequencies associated with the second derivative of the first filtered signal; and selecting the at least one acoustic frequency from the zero-crossing frequencies.

7. The method of claim 1, wherein the transmitting of the first acoustic transmit signal comprises transmitting the first acoustic transmit signal having a bandwidth of at least four kilohertz.

8. The method of claim 1, wherein the first acoustic transmit signal comprises at least one of the following:

an ultrasound signal having frequencies between approximately twenty kilohertz and two megahertz; or an audible signal having frequencies between approximately twenty hertz and twenty kilohertz.

9. The method of claim 1, wherein the performing of the audioplethysmography comprises:

transmitting a second acoustic transmit signal having the at least one acoustic frequency, the second acoustic transmit signal propagating within at least a portion of an ear canal of the user;

receiving a second acoustic receive signal, the second acoustic receive signal representing a version of the second acoustic transmit signal that has one or more waveform characteristics modified based on the propagation within the ear canal; and determining at least one physiological metric of the user based on the one or more modified waveform characteristics of the second acoustic receive signal.

10. The method of claim 9, wherein the determining of the at least one physiological metric of the user comprises:

demodulating the second acoustic receive signal by mixing a digital version of the second acoustic receive signal with a digital version of the second acoustic transmit signal to generate a second mixed signal;

passing the second mixed signal through a low-pass filter to generate a second filtered signal;

generating an autocorrelation of the second filtered signal; and determining a period of the autocorrelation of the second filtered signal to determine the at least one physiological metric.

11. The method of claim 9, wherein the at least one physiological metric comprises at least one of the following:

a heart rate of the user; or a respiration rate of the user.

12. A device comprising:

at least one speaker;

at least one microphone; and at least one processor, the device configured to:

perform, using the at least one speaker, the at least one microphone, and the at least one processor, a calibration process that identifies, from a set of multiple frequencies, at least one acoustic frequency suitable for audioplethysmography, the device is further configured to perform the following as part of the calibration process:

transmit, using the at least one speaker, a first acoustic transmit signal having the set of multiple frequencies, the first acoustic transmit signal propagating within at least a portion of an ear canal of a user;

receive, using the at least one microphone, a first acoustic receive signal, the first acoustic receive signal representing a version of the first acoustic transmit signal that has one or more waveform characteristics modified based on the propagation within the ear canal; and select, using the at least one processor, the at least one acoustic frequency from the set of multiple frequencies based on the one or more waveform characteristics; and perform, using the at least one speaker and the at least one microphone, the audioplethysmography at an ear of the user using the at least one acoustic frequency selected by the calibration process.

13. The device of claim 12, further comprising:

an active-noise-cancellation circuit comprising the at least one microphone.

14. The device of claim 13, wherein the at least one speaker and the at least one microphone are configured to be positioned proximate to one ear of a user.

15. The device of claim 12, wherein:

the at least one speaker is configured to be positioned proximate to a first ear of a user; and the at least one microphone is configured to be positioned proximate to a second ear.

16. The device of claim 12, wherein at least one of the at least one speaker or the least one microphone is part of at least one transducer of the device.

17. The device of claim 12, wherein the device is configured to at least partially seal one or more ears of a user.

18. The device of claim 12, wherein the device comprises:
at least one earbud; or
headphones.

19. The device of claim 12, wherein the at least one frequency comprises two or more frequencies from the set of multiple frequencies.

20. The device of claim 12, wherein the device is further configured to:

demodulate the first acoustic receive signal by mixing a digital version of the first acoustic receive signal with a digital version of the first acoustic transmit signal to generate a first mixed signal;

pass the first mixed signal through a low-pass filter to generate a first filtered signal;

determine, using the at least one processor, a second derivative of the first filtered signal;

identify, using the at least one processor, zero-crossing frequencies associated with the second derivative of the first filtered signal; and select, using the at least one processor, the at least one acoustic frequency from the zero-crossing frequencies.

* * * * *